United States Patent
Hancock et al.

(10) Patent No.: US 10,188,455 B2
(45) Date of Patent: Jan. 29, 2019

(54) ELECTROSURGICAL APPARATUS FOR GENERATING RADIOFREQUENCY ENERGY AND MICROWAVE ENERGY FOR DELIVERY INTO BIOLOGICAL TISSUE

(71) Applicant: Creo Medical Limited, Chepstow, Monmouthshire (GB)

(72) Inventors: Christopher Paul Hancock, Bath (GB); Malcolm White, Chepstow (GB); Nuwan Dharmisiri, Chepstow (GB)

(73) Assignee: CREO MEDICAL LIMITED, Cheptstow, Monmouthshire (GB)

( * ) Notice: Subject to any disclaimer, the term of this patent is extended or adjusted under 35 U.S.C. 154(b) by 239 days.

(21) Appl. No.: 15/102,845

(22) PCT Filed: Dec. 4, 2014

(86) PCT No.: PCT/GB2014/053597
§ 371 (c)(1),
(2) Date: Jun. 8, 2016

(87) PCT Pub. No.: WO2015/087051
PCT Pub. Date: Jun. 18, 2015

(65) Prior Publication Data
US 2016/0374752 A1 Dec. 29, 2016

(30) Foreign Application Priority Data
Dec. 9, 2013 (GB) .................. 1321710.4

(51) Int. Cl.
*A61B 18/14* (2006.01)
*A61B 18/18* (2006.01)
(Continued)

(52) U.S. Cl.
CPC ...... *A61B 18/1482* (2013.01); *A61B 18/1492* (2013.01); *A61B 18/1815* (2013.01);
(Continued)

(58) Field of Classification Search
CPC ...... H01P 5/12; H01P 1/36; H01P 5/08; H01P 5/103; A61B 2018/1823;
(Continued)

(56) References Cited

U.S. PATENT DOCUMENTS 4,091,344 A   5/1978   Latourrette
5,372,596 A * 12/1994   Klicek .................. A61B 18/12
                                                       606/34
(Continued)

FOREIGN PATENT DOCUMENTS

GB   2 486 343 A   6/2012
GB   2506377 A     4/2014
(Continued)

OTHER PUBLICATIONS

British Search and Examination Report of related British Patent Application No. GB1421526.3 dated May 26, 2015.
(Continued)

*Primary Examiner* — Jaymi Della
(74) *Attorney, Agent, or Firm* — Arent Fox LLP

(57) ABSTRACT

An isolating circuit for an electrosurgical generator arranged to produce radiofrequency (RF) energy and microwave energy for treating biological tissues is provided. The generator has an RF channel and a microwave channel which are combined at a signal combiner to enable the RF energy and microwave energy to be delivered into tissues along a common feed path. The isolating circuit includes a tunable wavelength isolator at a junction between the microwave channel and the signal combiner, and can include a capacitive structure between a ground conductor of the signal combiner and a conductive input section of the waveguide isolator to inhibit coupling of the RF energy and leakage of the microwave energy. The isolating circuit can combine into a single tunable unit all the necessary components to
(Continued)

isolate the microwave and RF channels from one another while providing a high withstanding voltage.

32 Claims, 5 Drawing Sheets

(51) Int. Cl.
*H01P 1/36* (2006.01)
*H01P 5/08* (2006.01)
*H01P 5/12* (2006.01)
*A61B 18/00* (2006.01)
*H01P 1/207* (2006.01)
*H01P 5/103* (2006.01)
*A61B 18/12* (2006.01)

(52) U.S. Cl.
CPC .............. *H01P 1/36* (2013.01); *H01P 5/08* (2013.01); *H01P 5/12* (2013.01); *A61B 2018/0063* (2013.01); *A61B 2018/00327* (2013.01); *A61B 2018/00494* (2013.01); *A61B 2018/00577* (2013.01); *A61B 2018/00601* (2013.01); *A61B 2018/00607* (2013.01); *A61B 2018/00642* (2013.01); *A61B 2018/00702* (2013.01); *A61B 2018/00755* (2013.01); *A61B 2018/00785* (2013.01); *A61B 2018/00869* (2013.01); *A61B 2018/00994* (2013.01); *A61B 2018/128* (2013.01); *A61B 2018/1273* (2013.01); *A61B 2018/1293* (2013.01); *A61B 2018/1823* (2013.01); *A61B 2018/1861* (2013.01); *A61B 2018/1876* (2013.01); *A61B 2018/1892* (2013.01); *H01P 1/207* (2013.01); *H01P 5/103* (2013.01)

(58) Field of Classification Search
CPC .... A61B 2018/1815; A61B 2018/1876; A61B 2018/00869; A61B 2018/00785; A61B 2018/00755; A61B 2018/1273; A61B 2018/128; A61B 18/1815
See application file for complete search history.

(56) References Cited

U.S. PATENT DOCUMENTS

| | | | |
|---|---|---|---|
| 6,582,427 B1* | 6/2003 | Goble | ............... A61B 18/042 |
| | | | 606/34 |
| 2002/0007912 A1* | 1/2002 | Kamarehi | ......... H01J 37/32192 |
| | | | 156/345.12 |
| 2004/0186470 A1 | 9/2004 | Goble et al. | |
| 2006/0155270 A1* | 7/2006 | Hancock | ............... A61B 18/18 |
| | | | 606/33 |
| 2010/0168727 A1* | 7/2010 | Hancock | ............... A61B 18/18 |
| | | | 606/33 |
| 2010/0278197 A1 | 11/2010 | Di et al. | |
| 2011/0121735 A1* | 5/2011 | Penny | ............... A61B 18/042 |
| | | | 315/111.21 |
| 2011/0208179 A1* | 8/2011 | Prakash | ............ A61B 18/1477 |
| | | | 606/33 |
| 2012/0098351 A1* | 4/2012 | Ross | ................ A61B 18/1233 |
| | | | 307/104 |
| 2013/0267943 A1* | 10/2013 | Hancock | .............. A61B 18/042 |
| | | | 606/33 |

FOREIGN PATENT DOCUMENTS

| | | |
|---|---|---|
| JP | 2007-526063 A | 9/2007 |
| JP | 2010-505572 A | 2/2010 |
| JP | H09-38102 A | 2/2010 |
| JP | 2011-172935 A | 9/2011 |
| WO | 2008/043999 A2 | 4/2008 |

OTHER PUBLICATIONS

British Search Report of related British Patent Application No. GB1321710.4 dated Jul. 14, 2014.
International Search Report and Written Opinion of related International Application No. PCT/GB2014/053597 dated Feb. 20, 2015.
Japanese Office Action of related Japanese Patent Application No. 2016-536861 dated Aug. 14, 2018.

* cited by examiner

ELECTROSURGICAL APPARATUS FOR GENERATING RADIOFREQUENCY ENERGY AND MICROWAVE ENERGY FOR DELIVERY INTO BIOLOGICAL TISSUE

CROSS-REFERENCE TO RELATED APPLICATIONS

This application is a National Stage entry of International Application No. PCT/GB2014/053597, filed Dec. 4, 2014, which claims priority to British Patent Application No. 1321710.4, filed Dec. 9, 2013. The disclosures of the priority applications are incorporated in their entirety herein by reference.

FIELD OF THE INVENTION

The invention relates to electrosurgical apparatus in which radiofrequency energy is used to treat biological tissue. In particular, the invention relates to surgical apparatus capable of generating radiofrequency (RF) energy for cutting tissue, It may be used in as part of a surgical apparatus which also delivers microwave frequency energy for haemostasis (i.e. sealing broken blood vessels by promoting blood coagulation).

BACKGROUND TO THE INVENTION

Surgical resection is a means of removing sections of organs from within the human or animal body. Such organs may be highly vascular. When tissue is cut (divided or transected) small blood vessels called arterioles are damaged or ruptured. Initial bleeding is followed by a coagulation cascade where the blood is turned into a clot in an attempt to plug the bleeding point. During an operation, it is desirable for a patient to lose as little blood as possible, so various devices have been developed in an attempt to provide blood free cutting. For endoscopic procedures, it is also undesirable for a bleed to occur and not to be dealt with as soon as quickly as possible, or in an expedient manner, since the blood flow may obscure the operator's vision, which may lead to the procedure needing to be terminated and another method used instead, e.g. open surgery.

Electrosurgical generators are pervasive throughout hospital operating theatres, for use in open and laparoscopic procedures, and are also increasingly present in endoscopy suites. In endoscopic procedures the electrosurgical accessory is typically inserted through a lumen inside an endoscope. Considered against the equivalent access channel for laparoscopic surgery, such a lumen is comparatively narrow in bore and greater in length. In the case of a bariatric patient the surgical accessory may have a length of 300 mm from handle to RF tip, whereas the equivalent distance in a laparoscopic case can be in excess of 2500 mm.

Instead of a sharp blade, it is known to use radiofrequency (RF) energy to cut biological tissue. The method of cutting using RF energy operates using the principle that as an electric current passes through a tissue matrix (aided by the ionic contents of the cells and the intercellular electrolytes), the impedance to the flow of electrons across the tissue generates heat. When an RF voltage is applied to the tissue matrix, enough heat is generated within the cells to vaporise the water content of the tissue. As a result of this increasing desiccation, particularly adjacent to the RF emitting region of the instrument (referred to herein as an RF blade) which has the highest current density of the entire current path through tissue, the tissue adjacent to the cut pole of the RF blade loses direct contact with the blade. The applied voltage is then appears almost entirely across this void which ionises as a result, forming a plasma, which has a very high volume resistivity compared to tissue. This differentiation is important as it focusses the applied energy to the plasma that completed the electrical circuit between the cut pole of the RF blade and the tissue. Any volatile material entering the plasma slowly enough is vaporised and the perception is therefore of a tissue dissecting plasma.

GB 2 486 343 discloses a control system for an electrosurgical apparatus which delivers both RF and microwave energy to treat biological tissue. The energy delivery profile of both RF energy and microwave energy delivered to a probe is set based on sampled voltage and current information of RF energy conveyed to the probe and sampled forward and reflected power information for the microwave energy conveyed to and from the probe.

FIG. 1 shows a schematic diagram of an electrosurgical apparatus 400 as set out in GB 2 486 343. The apparatus comprises a RF channel and a microwave channel. The RF channel contains components for generating and controlling an RF frequency electromagnetic signal at a power level suitable for treating (e.g. cutting or desiccating) biological tissue. The microwave channel contains components for generating and controlling a microwave frequency electromagnetic signal at a power level suitable for treating (e.g. coagulating or ablating) biological tissue.

The microwave channel has a microwave frequency source 402 followed by a power splitter 424 (e.g. a 3 dB power splitter), which divides the signal from the source 402 into two branches. One branch from the power splitter 424 forms a microwave channel, which has a power control module comprising a variable attenuator 404 controlled by controller 406 via control signal $V_{10}$ and a signal modulator 408 controlled by controller 406 via control signal $V_{11}$, and an amplifier module comprising drive amplifier 410 and power amplifier 412 for generating forward microwave EM radiation for delivery from a probe 420 at a power level suitable for treatment. After the amplifier module, the microwave channel continues with a microwave signal coupling module (which forms part of a microwave signal detector) comprising a circulator 416 connected to deliver microwave EM energy from the source to the probe along a path between its first and second ports, a forward coupler 414 at the first port of the circulator 416, and a reflected coupler 418 at the third port of the circulator 416. After passing through the reflected coupler, the microwave EM energy from the third port is absorbed in a power dump load 422. The microwave signal coupling module also includes a switch 415 operated by the controller 406 via control signal $V_{12}$ for connecting either the forward coupled signal or the reflected coupled signal to a heterodyne receiver for detection The other branch from the power splitter 424 forms a measurement channel. The measurement channel bypasses the amplifying line-up on the microwave channel, and hence is arranged to deliver a low power signal from the probe. In this embodiment, a primary channel selection switch 426 controlled by the controller 406 via control signal $V_{13}$ is operable to select a signal from either the microwave channel or the measurement channel to deliver to the probe. A high band pass filter 427 is connected between the primary channel selection switch 426 and the probe 420 to protect the microwave signal generator from low frequency RF signals.

The measurement channel includes components arranged to detect the phase and magnitude of power reflected from the probe, which may yield information about the material e.g. biological tissue present at the distal end of the probe. The measurement channel comprises a circulator 428 connected to deliver microwave EM energy from the source 402 to the probe along a path between its first and second ports. A reflected signal returned from the probe is directed into the third port of the circulator 428. The circulator 428 is used to provide isolation between the forward signal and the reflected signal to facilitate accurate measurement. However, as the circulator does not provide complete isolation between its first and third ports, i.e. some of the forward signal may break through to the third port and interfere with the reflected signal, a carrier cancellation circuit is used that injects a portion of the forward signal (from forward coupler 430) back into the signal coming out of the third port (via injection coupler 432). The carrier cancellation circuit include a phase adjustor 434 to ensure that the injected portion is 180° out of phase with any signal that breaks through into the third port from the first port in order to cancel it out. The carrier cancellation circuit also include a signal attenuator 436 to ensure that the magnitude of the injected portion is the same as any breakthrough signal.

To compensate for any drift in the forward signal, a forward coupler 438 is provided on the measurement channel. The coupled output of the forward coupler 438 and the reflected signal from the third port of the circulator 428 are connected to respective input terminal of a switch 440, which is operated by the controller 406 via control signal $V_{14}$ to connect either the coupled forward signal or the reflected signal to a heterodyne receiver for detection.

The output of the switch 440 (i.e. the output from the measurement channel) and the output of the switch 415 (i.e. the output from the microwave channel) are connect to a respective input terminal of a secondary channel selection switch 442, which is operable by the controller 406 via control signal $V_{15}$ in conjunction with the primary channel selection switch to ensure that the output of the measurement channel is connected to the heterodyne receiver when the measurement channel is supplying energy to the probe and that the output of the microwave channel is connected to the heterodyne receiver when the microwave channel is supplying energy to the probe.

The heterodyne receiver is used to extract the phase and magnitude information from the signal output by the secondary channel selection switch 442. A single heterodyne receiver is shown in this system, but a double heterodyne receiver (containing two local oscillators and mixers) to mix the source frequency down twice before the signal enters the controller may be used if necessary. The heterodyne receiver comprises a local oscillator 444 and a mixer 448 for mixing down the signal output by the secondary channel selection switch 442. The frequency of the local oscillator signal is selected so that the output from the mixer 448 is at an intermediate frequency suitable to be received in the controller 406. Band pass filters 446, 450 are provided to protect the local oscillator 444 and the controller 406 from the high frequency microwave signals.

The controller 406 receives the output of the heterodyne receiver and determines (e.g. extracts) from it information indicative of phase and magnitude of the forward and/or reflected signals on the microwave or measurement channel. This information can be used to control the delivery of high power microwave EM radiation on the microwave channel or high power RF EM radiation on the RF channel. A user may interact with the controller 406 via a user interface 452, as discussed above.

The RF channel shown in FIG. 1 comprises an RF frequency source 454 connected to a gate driver 456 that is controlled by the controller 406 via control signal $V_{16}$. The gate driver 456 supplies an operation signal for an RF amplifier 458, which is a half-bridge arrangement. The drain voltage of the half-bridge arrangement is controllable via a variable DC supply 460. An output transformer 462 transfers the generated RF signal on to a line for delivery to the probe 420. A low pass, band pass, band stop or notch filter 464 is connected on that line to protect the RF signal generator from high frequency microwave signals.

A current transformer 466 is connected on the RF channel to measure the current delivered to the tissue load. A potential divider 468 (which may be tapped off the output transformer) is used to measure the voltage. The output signals from the potential divider 468 and current transformer 466 (i.e. voltage outputs indicative of voltage and current) are connected directly to the controller 406 after conditioning by respective buffer amplifiers 470, 472 and voltage clamping Zener diodes 474, 476, 478, 480 (shown as signals B and C in FIG. 1).

To derive phase information, the voltage and current signals (B and C) are also connected to a phase comparator 482 (e.g. an EXOR gate) whose output voltage is integrated by RC circuit 484 to produce a voltage output (shown as A in FIG. 1) that is proportional to the phase difference between the voltage and current waveforms. This voltage output (signal A) is connected directly to the controller 406.

The microwave/measurement channel and RF channel are connected to a signal combiner 114, which conveys both types of signal separately or simultaneously along cable assembly 116 to the probe 420, from which it is delivered (e.g. radiated) into the biological tissue of a patient.

A waveguide isolator (not shown) may be provided at the junction between the microwave channel and signal combiner. The waveguide isolator may be configured to perform three functions: (i) permit the passage of very high microwave power (e.g. greater than 10 W); (ii) block the passage of RF power; and (iii) provide a high withstanding voltage (e.g. greater than 10 kV). A capacitive structure (also known as a DC break) may also be provided at (e.g. within) or adjacent the waveguide isolator. The purpose of the capacitive structure is to reduce capacitive coupling across the isolation barrier.

SUMMARY OF THE INVENTION

The present invention provides an enhancement to the electrosurgical apparatus disclosed GB 2 486 343. The enhancement concerns improving the accuracy of reflected power measurements by reducing the insertion losses within the microwave and RF channels.

At its most general, the present invention provides a tunable waveguide isolator at the junction between the microwave channel and signal combiner. In a preferred embodiment, the invention combines into a single tunable unit all the necessary components to isolate the microwave and RF channels from one another whilst providing a high withstanding voltage (e.g. greater than 10 kV). The impedance of the waveguide isolator may be tuned in situ (i.e. when the apparatus is ready for use) or in advance to reduce the return losses experienced along the signal pathways and hence improve measurement sensitivity.

The invention may provide a capacitive structure at or adjacent the tunable waveguide isolator that can reduce capacitive coupling across the isolation barrier. The reduced capacitive coupling may be provided by connecting the waveguide isolator (in particular the outer conductor of the waveguide isolator) in series with an additional capacitive component, such as a coaxial isolator. To maintain the reduced capacitive coupling during operation, the additional capacitive component may have a high breakdown voltage, e.g. 500 V or more. Thus, the waveguide isolator and additional capacitive component (e.g. coaxial isolator) may act in combination as a low frequency blocking filter to prevent RF EM radiation from the RF channel from entering the microwave channel.

Alternatively, in a preferred embodiment the capacitive structure may be an integral part of the DC isolation barrier in the waveguide isolator itself. For example, reduced capacitive coupling can be achieved by decreasing the capacitance or increasing the capacitive reactance of the isolating gap formed in the outer conductor of the waveguide isolator, e.g. by increasing the thickness of insulating material present in the gap. In this arrangement, the waveguide isolator may include a choke to minimise leakage of microwave power at the gap.

Thus, according to the invention, there is provided an electrosurgical apparatus for resection of biological tissue, the apparatus comprising: a radiofrequency (RF) signal generator for generating RF electromagnetic (EM) radiation having a first frequency; a microwave signal generator for generating microwave EM radiation having a second frequency that is higher than the first frequency; a probe arranged to deliver the RF EM radiation and the microwave EM radiation separately or simultaneously from a distal end thereof; and a feed structure for conveying the RF EM radiation and the microwave EM radiation to the probe, the feed structure comprising an RF channel for connecting the probe to the RF signal generator, and a microwave channel for connecting the probe to the microwave signal generator, wherein the RF channel and microwave channel comprise physically separate signal pathways from the RF signal generator and microwave signal generator respectively, wherein the feed structure includes a combining circuit having a first input connected to the separate signal pathway on the RF channel, a second input connected to the separate signal pathway on the microwave channel, and an output connected to a common signal pathway for conveying the RF EM radiation and the microwave EM radiation separately or simultaneously along a single channel to the probe, wherein the microwave channel includes a waveguide isolator connected to isolate the separate signal pathway on the microwave channel from the RF EM radiation, and wherein the waveguide isolator has an adjustable impedance.

The adjustable impedance of the waveguide isolator permits the return loss to be reduced in a manner that improves the measurement sensitivity of the apparatus. The adjustable impedance may be provided in any suitable manner. For example, the waveguide isolator may include a tuning portion that is adjustable to change the impedance of the waveguide isolator. The tuning portion may be a tuning unit comprising a plurality of tuning stubs that are adjustably insertable into the waveguide isolator.

The tunable nature of the waveguide isolator is particular advantageous when the waveguide isolator also acts as a DC break and as the combining circuit.

Thus, the waveguide isolator may comprise a conductive input section, a conductive output section which mates with the input section to define a waveguide cavity within a volume enclosed by the input and output sections, and a DC isolation barrier arranged between the input and output sections, wherein the output on the common signal pathway includes a signal conductor and a ground conductor, and wherein the feed structure includes a capacitive structure between the ground conductor of the output on the common signal pathway and the conductive input section of the waveguide isolator, the capacitive structure being arranged to inhibit coupling of the RF EM energy and leakage of the microwave EM energy.

The capacitive structure may be provided by the DC isolation barrier and a microwave choke formed on the input section of the waveguide isolator. Where the inner and outer sections of the waveguide isolator define a cylindrical body, the microwave choke may comprise an annular channel extending axially from the distal end of the inner section of the waveguide isolator. The channel may be filled with air or another suitable dielectric. The axial length of the choke may be a quarter wavelength of the microwave EM energy (or an odd multiple thereof) in the material (e.g. air) and geometrical structure of the channel.

The DC isolation barrier itself may include a rigid insulating spacer element mounted between the inner and outer sections of the waveguide isolator. The spacer element may be formed from an insulating plastic, such as Delrin® or polyvinylchloride (PVC). In the waveguide is cylindrical, the spacer element may comprise an annular sleeve mounted over the distal end of one of the input or output sections of the waveguide isolator. The outer surface of the sleeve may be flush with the outer surface of the input and output sections.

The axial length of the overlap between the sleeve and the inner and/or outer sections is preferably an odd number of quarter wavelengths (usually one quarter wavelength) at the microwave frequency in the material of the sleeve and the structure containing it. The thickness of the insulating layer (radial thickness when it is an insulating sleeve) may be selected to be either as thin as possible to minimise microwave leakage or as thick as necessary to reduce the capacitance to a level that provides the required isolation at the frequency of the RF EM energy. These two requirements are in conflict and it may be that they cannot both be met. In practice, the sleeve may thus comprise either (i) a thin insulating layer, which meets the microwave leakage requirement but requires an additional capacitive break in series with the outer conductor in order to reduce the capacitance (e.g. the coaxial isolator discussed below), or (ii) a thick insulating layer, which meets the RF REM energy isolation requirement, but requires an additional microwave component to achieve the required low microwave leakage (e.g. the microwave choke discussed above).

The DC isolation barrier may includes additional components. For example, the DC isolation barrier may include an insulating film mounted on a portion of the inner surface of the input section at the junction with the rigid insulating spacer element. The insulating film may extend away from the rigid insulating spacer element by a predetermined distance, e.g. to increase the surface breakdown voltage.

The waveguide isolator allows the combining circuit to float electrically, which increases safety. The capacitive structure acts to increase the capacitive reactance of the combining circuit to reduce the risk of an RF signal escaping down the microwave channel via a capacitive coupling through the waveguide isolator.

In an embodiment where the combining circuit is integrated with the waveguide isolator, the separate signal pathway on the RF channel may terminate at an RF connector which is connected into the waveguide isolator, whereby the RF signal is directly conveyed to an output port of the waveguide isolator. The common signal pathway may thus extend away from the output port of the waveguide isolator. Thus, the output connected to common signal pathway may include an output probe mounted on the output section of the waveguide isolator, the output probe having a coupling conductor extending into the waveguide isolator to couple the microwave EM energy therefrom. The first input may include an RF connector mounted on the waveguide isolator, the RF connector having a signal conductor that extends into the waveguide cavity to electrically contact the coupling conductor of the output probe. The signal conductor may be an insulated conductive wire or rod. The signal conductor may contact the coupling conductor at a predetermined distance from its tip. The distance may be adjustable, e.g. by changing the position of the RF connected with respect to the waveguide isolator. Preferably the position of the signal conductor is selected to that it closely follows (e.g. is substantially aligned with) an equipotential of the microwave EM field within the microwave isolator, so the presence of the RF connector does not affect the behaviour of the microwave EM energy. Aligning the signal conductor in this way means that the amount of microwave EM energy that can leak into the RF connector is minimal. However, as a further barrier to leakage, a microwave choke may be mounted on the RF connector to prevent the microwave EM energy from leaking out of the waveguide isolator through the signal conductor of the RF connector. The microwave choke may be radial or cylindrical, or any other suitable shape. Its dimensions are chosen appropriately based on the wavelength of the microwave EM energy.

In order to maintain a high breakdown voltage, portions of the signal conductor and coupling conductor adjacent the walls of the waveguide isolator may be surrounded by an insulating material, e.g. a suitable dielectric. Thus, a proximal portion of the coupling conductor of the output probe that extends into the waveguide isolator may be surrounded by an insulating sleeve. And a proximal portion of the signal conductor of the RF connector that extends into the waveguide isolator may be surrounded by an insulating sleeve.

Integrating the combining circuit with the adapted waveguide isolator provides a single component which provides the necessary generator-to-patient isolation whilst avoiding unwanted RF coupling and microwave leakage. In addition this single component obviates the need for a separate multi-stub (low pass) rejection filter on the RF channel. Moreover, the integrated nature of the component means that the insertion loss of the device is much lower (there is no microstrip board, fewer interconnections, fewer microwave routing cables, no co-axial isolator). The ability to tune the waveguide isolator in situ further improves the insertion loss. The integrated waveguide isolator is also physically smaller and easier to manufacture than the multi-component solution.

In another embodiment, the capacitive structure may comprise an additional capacitance connected in series with the tunable waveguide isolator. The additional capacitance may be a coaxial isolator. The additional capacitance may have a high breakdown voltage to cope with the peak voltages seen within the system. The breakdown voltage of the additional capacitance may be 1 kV or more, preferably 2 kV or more.

The separate signal pathway on the RF channel may be isolated from the microwave EM radiation. The RF channel may therefore include an isolator, e.g. a low pass, band pass, band stop or notch filter, connected between the separate signal pathway on the RF channel and the combining circuit. The low pass, band pass, band stop or notch filter may be integrated with the combining circuit. For example, in one embodiment, the combining circuit may comprise a T-shaped open microstrip bi-direction diplexer circuit having a low pass, band pass, band stop or notch filter integrally formed therewith to prevent microwave EM radiation from leaking out of the first input. The band stop filter may comprise a plurality of stubs (e.g. two, three or four stubs) formed on the microstrip line between the first input and T-junction of the diplexer circuit.

Using the adapted waveguide isolator mentioned above or the series-connected waveguide isolator and coaxial isolator as a high pass filter may overcome three disadvantages of using a single high frequency capacitor to provide the necessary isolation. Firstly, it is desirable for the entire combining circuit to be floating, i.e. without a direct path to ground or the mains power. Thus, both the signal and ground planes from the microwave channel need to enter the combining circuit capacitively. The waveguide isolator can provide this property. Secondly, it is desirable to prevent the RF signal from leaking out to the patient or user through capacitive coupling across the waveguide isolator. The adapted DC isolation barrier described above or the coaxial isolator can provide the necessary capacitance to increase the capacitive reactance of the junction and hence inhibit the capacitive coupling at the first frequency. A coaxial isolator is preferred to a normal capacitor because the RF signal may be supplied as high voltage pulses (e.g. of 5 kV or higher), which is higher than the typical voltage breakdown of a normal capacitor. Thirdly, the insertion loss of the series arrangement is much lower than for a normal capacitor at the preferred microwave frequencies disclosed herein (e.g. 5.8 GHz or higher), which can help to prevent the circuit resonating a certain frequencies.

The invention may be combined with any or all of the components (either individually or in any combination) described above with reference to the electrosurgical apparatus 400 as set out in GB 2 486 343. For example, the RF channel and microwave channel may include any or all of the components of the RF channel and microwave channel respectively described above. As mentioned above, the microwave channel may include a circulator for separating the a reflected signal on the microwave channel from a forward signal. In an alternative embodiment, a directional coupler may be used for the same purpose. In practice, the circulator or directional coupler will exhibit imperfect isolation, which in turn affects the reflected signal that is actually received at the detector. The adjustable impedance of the invention is capable of compensating for this imperfect isolation as well as optimising return loss and transmission in the waveguide isolator.

The apparatus may include a controller operable to select an energy delivery profile for the RF EM radiation and the microwave EM radiation. Herein, energy delivery profile may mean the shape of the waveform in terms of voltage/current and time for the RF energy and power level and time for the microwave energy. Control of the energy delivery profile can permit a range of therapeutic applications to be realised.

The apparatus may include an RF signal detector for sampling current and voltage on the RF channel and generating therefrom a RF detection signal indicative of the phase difference between the current and voltage. The controller may be in communication with the RF signal detector to receive the RF detection signal and select the energy delivery profile for the RF EM radiation based on the RF detection signal.

Similarly, the apparatus may include a microwave signal detector for sampling forward and reflected power on the microwave channel and generating therefrom a microwave detection signal indicative of the magnitude and/or phase of microwave power delivered by the probe. The controller may be in communication with the microwave signal detector to receive the microwave detection signal and select the energy delivery profile for the microwave EM radiation based on the microwave detection signal.

Thus, the system may be configured to provide secure control over the output of the electrosurgical apparatus. For example, the apparatus may enable selection of an energy delivery profile for tissue cutting which may comprise delivering continuous wave (CW) RF EM energy with a 400 V peak amplitude at a power level of 30 W. The controller may be adjustable (e.g. manually adjustable) to vary the peak amplitude and power level. Because the RF and microwave EM radiation are monitored, the energy delivered to the tissue can be determined with accuracy. In another example, the apparatus may enable selection of an energy delivery profile for coagulation may comprise delivering continuous wave (CW) microwave EM energy at a power level of 25 W. Again, the controller may be adjustable (e.g. manually adjustable) to vary the power level.

More generally, to achieve tissue cutting in a dry environment, it may be necessary to deliver a 500 kHz continuous wave sinusoidal waveform with a peak voltage of amplitude 400 V and a power setting of 40 W, whereas to achieve tissue cutting in a wet environment, it may be necessary to deliver one or more bursts of 500 kHz energy with a peak voltage of 4000 V with a peak power of 200 W and a duty cycle of 10%, which may be set up in the form whereby the ON time is 10 ms and the OFF time is 90 ms. This kind of pulsed energy delivery profile may ensure that the energy is passed to the tissue rather than causing undesirable heating of the surrounding fluid. For efficient tissue coagulation in dry tissue, CW microwave power may be delivered into tissue at an RMS power level of 30 W. For coagulation in a wet environment, the microwave power may be pulsed, e.g. having a peak power of 100 W with a 30% duty cycle.

Other waveforms that produce desirable therapeutic tissue affects may include a combination of RF and microwave energy delivered in CW and pulsed formats similar to those described above. The RF and microwave energy may be delivered simultaneously where the microwave energy modulates the RF energy. For example, a 400 V peak 500 kHz CW RF profile may be modulated with a 10 W CW 5.8 GHz microwave signal to produce a degree of tissue coagulation during the resection process to reduce bleeding when an organ or a section of an organ is being removed.

All waveform parameters may be adjustable by the controller, e.g. via a user interface.

The control system may comprise a dedicated measurement channel, for delivering energy (preferably microwave energy) at a low power level (e.g. 10 mW or less). The system may thus make available measurement signals from a channel that is not delivering therapeutic effects, i.e. the waveform or energy delivery into tissue may be controlled based on low power measurements made using a channel that is not involved in delivering therapeutic tissue effects. The measurement channel may be use the same source as the microwave channel. The system may be switchable so that microwave energy is delivered either through the measurement channel (in a "measurement mode") or through the microwave channel (in a "treatment mode"). Alternatively, the microwave channel may be switchable between a low power mode (for measurement) and a high power mode (for treatment). In this arrangement a separate measurement channel is not needed.

The system may be configured to supply energy for cutting and coagulating tissue simultaneously (e.g. a mixed or blend mode) or may be operated independently, whereby the RF and microwave energy is delivered to the probe under manual user control (e.g. based on the operation of a footswitch pedal) or automatically based on measured phase and/or magnitude information from the RF and/or microwave channel. The system may be used to perform tissue ablation and cutting. In the instance where microwave and RF energy are delivered simultaneously, either or both RF and microwave energy returned to the respective generators may be used at high power or low power to control the energy delivery profile. In this instance, it may be desirable to take measurements during the OFF time when the energy delivery format is pulsed.

The distal end of the probe may comprise a bipolar emitting structure comprising a first conductor spatially separated from a second conductor, the first and second conductors being arranged to act: as active and return electrodes respectively to convey the RF EM radiation by conduction, and as an antenna or transformer to facilitate radiation of the microwave EM energy. Thus, the system may be arranged to provide a local return path for RF energy. For example, the RF energy may pass by conduction through the tissue separating the conductors, or a plasma may be generated in the vicinity of the conductors to provide the local return path. RF tissue cutting may be produced by a fixed dielectric material separating the first and second conductors, where the thickness of the dielectric material is small, i.e. less than 1 mm and the dielectric constant high, i.e. greater than that of air.

The invention may be particularly suitable in gastrointestinal (GI) procedures, e.g. to remove polyps on the bowel, i.e. for endoscopic sub-mucosal resection. The invention may also lend itself to precision endoscopic procedures, i.e. precision endoscopic resection, and may be used in ear, nose and throat procedures and liver resection.

The first frequency may be a stable fixed frequency in the range 10 kHz to 300 MHz and the second frequency may be a stable fixed frequency in the range 300 MHz to 100 GHz. The first frequency should be high enough to prevent the energy from causing nerve stimulation and low enough to prevent the energy from causing tissue blanching or unnecessary thermal margin or damage to the tissue structure. Preferred spot frequencies for the first frequency include any one or more of: 100 kHz, 250 kHz, 500 kHz, 1 MHz, 5 MHz. Preferred spot frequencies for the second frequency include 915 MHz, 2.45 GHz, 5.8 GHz, 14.5 GHz, 24 GHz. Preferably the second frequency is at least an order of magnitude (i.e. at least 10 times) higher than the first frequency.

In another aspect, the invention may be expressed as an isolating circuit for electrosurgical apparatus for resection of biological tissue, the isolating circuit comprising: a combining circuit having a first input connectable to receive radiofrequency (RF) electromagnetic (EM) radiation having a first frequency from an RF channel, a second input connectable to receive microwave EM radiation having a second frequency that is higher than the first frequency from a microwave channel, and an output in communication with the first and second inputs for conveying the RF EM radiation and the microwave EM radiation to a common signal pathway, and a waveguide isolator connected to isolate the microwave channel from the RF EM radiation, wherein the waveguide isolator comprises a conductive input section, a conductive output section which mates with the input section to define a waveguide cavity within a volume enclosed by the input and output sections, and a DC isolation barrier arranged between the input and output sections, wherein the output from the combining circuit includes a signal conductor and a ground conductor, wherein the isolating circuit comprises a capacitive structure between the ground conductor of the output from the combining circuit and the conductive input section of the waveguide isolator, the capacitive structure being arranged to inhibit coupling of the RF EM energy and leakage of the microwave EM energy, and wherein the waveguide isolator has an adjustable impedance. Features of the combining circuit, waveguide isolator and capacitive structure described above may also be applicable to this aspect of the invention.

Also disclosed herein are improvements to the amplifier module and microwave signal coupling module on the microwave channel. These improvements seek to provide one or more of higher power output, greater measurement sensitivity, and reduction of generator noise in the measurement signals.

A first improvement concerns the configuration of the amplifier module. In a preferred embodiment, the amplifier module comprises a drive amplifier whose output is split between four power amplifiers operating in parallel. The split occurs in two two-way splitter stages. The four power amplifiers may have a transistor power of 75 W and gain of 10 dB, which properties can be provided by a de-rated Mitsubishi MGFC50G5867. This configuration provides more than 1 dB headroom for thermal degradation of saturated output power. The set up may enable a total output power of greater than 120 W to be achieved.

A second improvement concerns the configuration of the microwave signal coupling module. In a preferred embodiment, a 4-port circulator is used, whereby the isolation and return loss of the circulator may be 20 dB or better.

A third improvement concerns the configuration of the reflected power coupler. In a preferred embodiment, a quadrature mixer is used to detect the reflected signal. This allows the vector sum of unwanted signals to be subtracted from the total signal received back from the probe, thereby enabling more accurate measurement than is possible with a square law detector.

A fourth improvement concerns the configuration of the amplifier module. In a preferred embodiment, the amplifier module includes a digital processor arranged to digitise the signals that are used for measurement before they are output from the amplifier module. This can ameliorate the effect of noise from the generator that can couple into analogue signals.

BRIEF DESCRIPTION OF THE DRAWINGS

A detailed discussion of the principles behind the invention and examples thereof is presented below with reference to the accompanying drawings, in which.

DETAILED DESCRIPTION; FURTHER OPTIONS AND PREFERENCES

Figure 1:
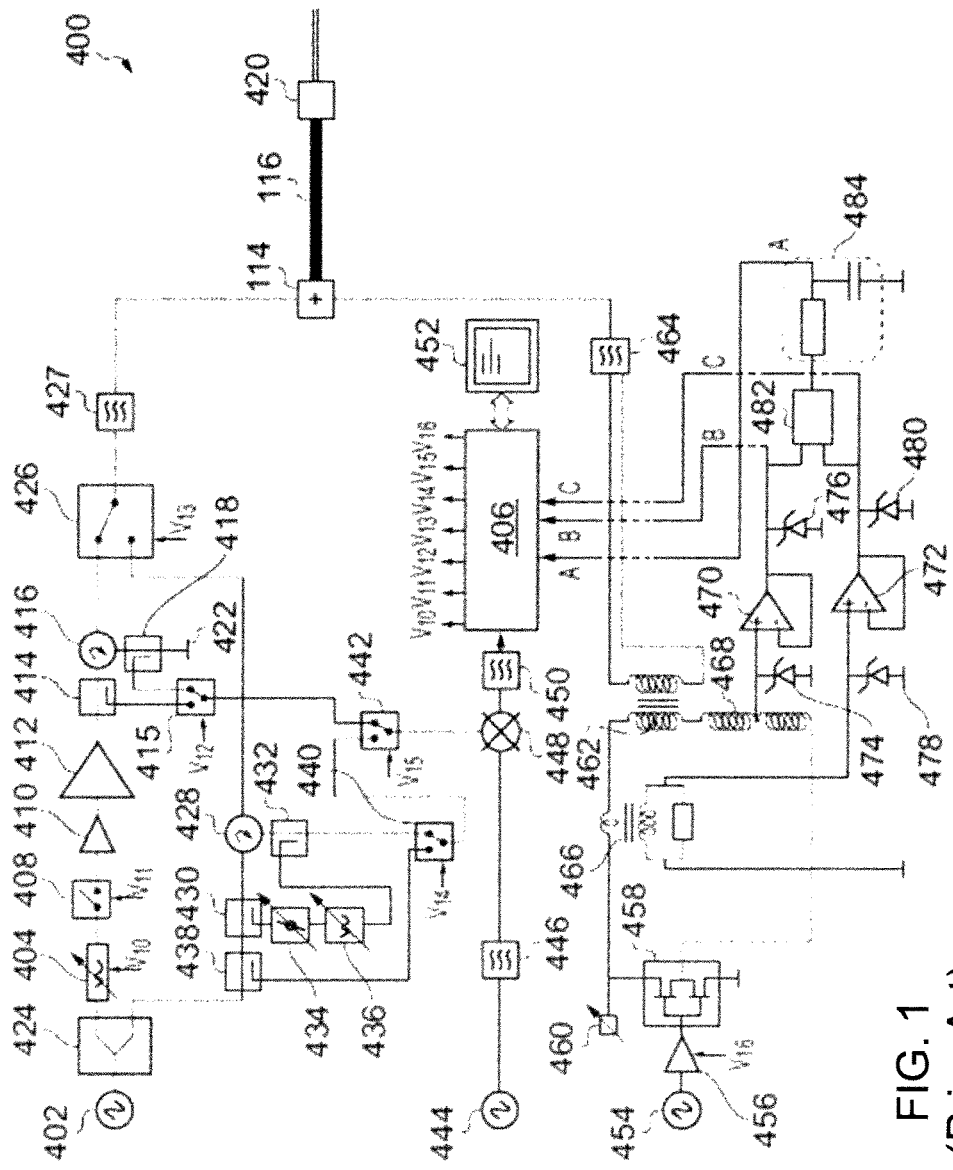
FIG. 1 is an overall schematic system diagram of an electrosurgical apparatus in which the present invention may be used, and is discussed above.

In operation, the electrosurgical apparatus with which the present invention is used aims to accurately measure the power reflected from the distal end of a coaxial cable, so that the presence of a tool can be detected, and also its performance evaluated.

Accurate measurement of the reflected power is made difficult by the attenuation in the cable, which is close to 7 dB each way, so that even a total reflection at the distal end would give a return loss of 14 dB (i.e. ¹⁄₂₅ of the power originally fed into the cable is returned from the cable). This magnifies the relative effect of unwanted power due to coupler inaccuracies, or due to reflections close to the detector, for instance, by a factor of 5.

A significant improvement could be made if a low attenuation cable were to be used. However, the available diameter in the endoscope channel imposes a maximum diameter on the coaxial cable, and the length of the endoscope imposes a minimum length for the cable, and the 7 dB attenuation is the best presently available.

In addition it should be remembered that at the microwave frequencies desired for use with the invention (i.e. preferably 5.8 GHz or more), the voltages and currents on the transmission line reverse every 18 mm so that the voltages from reflections at different places on the transmission line may not add but may instead subtract: in fact they must be added as vectors with direction (phase) as well as amplitude (voltage) being taken into account. In practice this means that the uncertainty in power associated with unwanted reflections is twice as large as might be expected by adding powers, and that unwanted reflections can not easily be subtracted from measurements to leave the desired signal, as both the voltage and the phase of the unwanted signal need to be known for it to be removed from the measurement.

The present disclosure discusses the source of the unwanted voltages, and identifies techniques that can be used to cancel them or reduce their effect on measurement accuracy.

The forward travelling wave in a line of impedance Z will be defined to have a voltage V and a power $V^2/Z$ (0 dB). The forward signal reaching the detector will be attenuated by the isolation of the circulator or the directivity of the coupler which will be represented by a power reduction by a ratio D (for a directivity of 20 dB, D=1/100), and a voltage reduction by a ratio $\sqrt{D}=\delta$. The phase of the transmitter signal reaching the detector will be defined to be zero. The complex voltage at the detector due to the transmitter breakthrough is then $V_F=V\delta\exp(-j0)=V\delta$.

The detector does not measure complex voltage, but will measure the magnitude of the sum of complex voltages that reach it. The complex voltage due to the forward breakthrough will be added to the complex voltage due to any reflected signal and the detector will give the magnitude of this sum.

The reflected signal will also be the sum of the reflection from the distal end of the cable, of any reflections from components before the cable, and of reflections from imperfections in the cable. A representative reflection of complex reflection coefficient $\Gamma_R$ from proportion p along the cable of length L (about 2 m) and delay length ηL (about 2.8 m) will be included in the calculation, as well as a reflection from the distal end with complex reflection coefficient $\Gamma_D$. The attenuation in the cable is α n/m which for the observed approximately 7 dB in a 2 m cable is 3.5 dB/m or α=3.5 ln(10)/20≈0.403 n/m.

Taking $k=2\pi/\lambda$, the free-space wavenumber of the microwave signal, and $\eta$, the reciprocal of the velocity factor of the cable, and allowing for an extra distance d through the isolator sections and couplers, the complex reflected signal at the detector is:

$$V_R = \{\Gamma_R \exp(-j2kp\eta L)\exp(-2\alpha pL) + \Gamma_D \exp(-j2k\eta L)\exp(-2\alpha L)\}\exp(-jkd).$$

Added to the breakthrough from the transmitter this becomes:

$$V_{TOT} = V_F + V_R$$
$$= V\begin{bmatrix} \delta + \{\Gamma_R \exp-(-j2kp\eta L)\exp(-2\alpha pL) + \\ \Gamma_D \exp(-j2k\eta L)\exp(-2\alpha L)\}\exp(-jkd) \end{bmatrix}$$

Ignoring the factor of V that multiplies everything in the last row of the equation, the first term in the square brackets $\delta$ is constant, and for 20 dB directivity is 0.1. This will be the measurement if there is a perfect load. The sizes of the next two terms are $\Gamma_R \exp(-2\alpha pL)$ and $\Gamma_D \exp(-2\alpha L)$ respectively. If the reflection causing the second term comes from the proximal end of the coaxial cable, then p=0 and the size of the second term becomes $\Gamma_R$. If the attenuation of the cable is 7 dB each way (or, more precisely, 6.99 dB) the size of the third term becomes $\Gamma_D/5$.

We now have, for example, $$V_{TOT} = V[0.1 + \{\Gamma_R + \Gamma_D \exp(-j2k\eta L)/5\}\exp(-jkd)],$$

where the terms on the right hand side are in the ratio $0.1:\Gamma_R:\Gamma_D/5$. For a well-made transmission line the second term will be very small, and should be smaller than the last term, but the first term is likely to be larger than the last term, which we hope to measure and will ideally be very small (we want it to be zero, i.e. ideally no power is reflected from the distal end). The fact that the last term is likely to be no bigger than the first term makes measuring it accurately more difficult.

The individual terms represent vectors. With the exception of the first term, which has been defined to be real (i.e. along the x-axis, with zero phase), the directions of the vectors are not certain, and depend on the complex reflection coefficients $\Gamma_R$ and $\Gamma_D$. Also, the exponential terms in this equation that contain j represent rotation of the vectors they multiply. At a frequency of 5.8 GHz, with a velocity factor of about 70% in coaxial cable, every 18 mm of cable results in 360 degrees rotation in the phase of the reflection, so differences in length of cables or position of defects as small as 1 mm can significantly affect the relative directions of the different vectors (20 degrees per mm).

Starting again with the equation for the total voltage:

$$V_{TOT} = V[0.1 + \{\Gamma_R + \Gamma_D \exp(-j2k\eta l)/5\}\exp(-jkd)].$$

The term in the curly brackets is the sum of a reflection at the proximal end of the cable and a reflection at the distal end of the cable. The sum can be represented by the vector $\Gamma_D/5$ rotated about the tip of the vector $\Gamma_R$. This will generate a circle which represents the locus of all possible results, for different phases of $\Gamma_D$ and $\Gamma_R$, and as little as 18 mm difference in the line length between them.

This is also the result that will be observed on a Vector Network Analyser (VNA) as the frequency is changed over about 50 MHz. This produces the typical periodic lumpy pattern that is obtained for return loss measurements of the tools. If the return loss of any defect near the proximal end of the cable is about 14 dB, then it is possible for the return from an unmatched cable (14 dB) to cancel it completely giving a total return loss better than 30 dB. In this case a better terminated cable (a well matched tool) will give a worse total return loss, the total return loss being dominated by the 14 dB return loss of the defect.

At the detector, the result of the addition of $\Gamma_R$ and $\Gamma_D/5$ is further rotated (by the last term in the square brackets) and will add to the 0.1 transmitter breakthrough with an uncertain phase. The resultant voltage may take any value between a maximum of $V(0.1+|\Gamma_R|+|\Gamma_D/5|)$ and a minimum of zero, or $V(0.1-|\Gamma_R|-|\Gamma_D/5|)$ if this is greater than zero.

Figure 2:
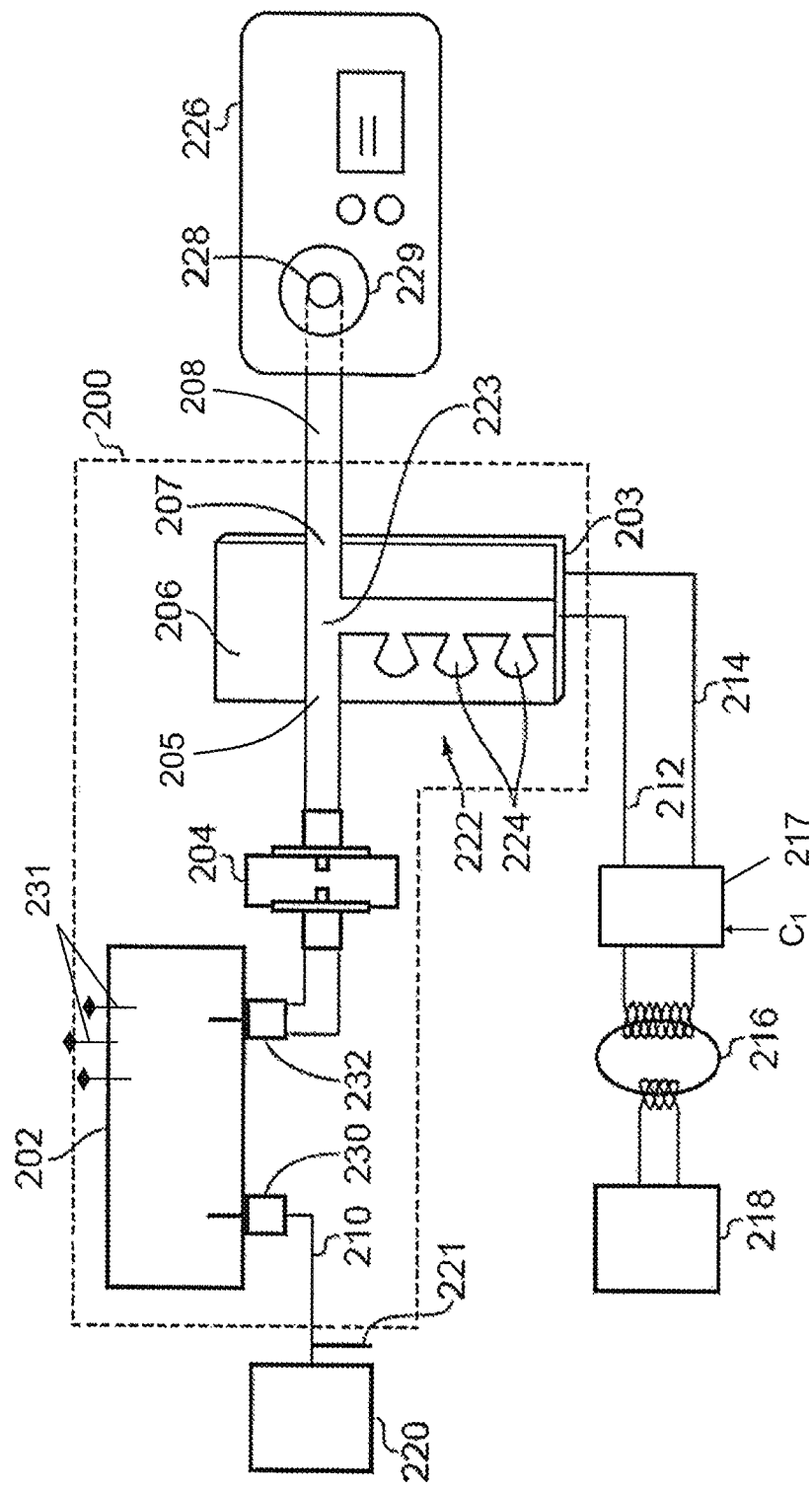
FIG. 2 is a schematic diagram of an isolating circuit in an electrosurgical apparatus that is an embodiment of the invention.

FIG. 2 is a schematic diagram of an isolating circuit 200 for an electrosurgical apparatus that is an embodiment of the invention. The isolating circuit 200 forms part of a feed structure for conveying RF EM radiation from an RF signal generator 218 and microwave radiation from a microwave signal generator 220 to a probe. In this embodiment, the probe (not shown) is connectable to an output port 228 provided in a housing 226. The feed structure comprises an RF channel having a RF signal pathway 212, 214 for conveying the RF EM radiation and a microwave channel having a microwave signal pathway 210 for conveying the microwave EM radiation. The signal pathways for the RF EM radiation and microwave radiation are physically separate from each other. The RF signal generator is connected to the RF signal pathway 212, 214 via a voltage transformer 216. The secondary coil of the transformer 216 (i.e. on the probe side of the arrangement) is floating, so there is not direct current path between the patient and the RF signal generator 218. This means that both the signal conductor 212 and ground conductor 214 of the RF signal pathway 212, 214 are floating.

A combining circuit 206 has a first input 203 for connecting to the RF signal pathway 212, 214, and a second input 205 for connecting to the microwave signal pathway 210. The combining circuit 206 joins the pathways to an output 207, which is connected to a common signal pathway 208. The common signal pathway 208, which may include a flexible cable (e.g. coaxial cable of the like) conveys the RF EM radiation and microwave EM radiation to the probe. In this embodiment the combining circuit 206 comprises a T-shaped microstrip junction formed on a low loss microwave dielectric substrate (e.g. a suitable type of RT/Duroid® substrate manufactured by Rogers Corporation). The ground plane of the microstrip junction, which is formed on the opposite side of the substrate from the T-shaped microstrip junction, is connected to the ground conductor 214 of the RF signal pathway 212, 214. It is therefore floating. The T-shaped microstrip junction provides the first input 203, which is connected to the signal conductor 212 of the RF signal pathway.

A band stop filter 222 is provided on the T-shaped microstrip junction in the form of three stubs 224 in shunt on the microstrip line between the first input 203 and junction 223 with the microwave microstrip line. The stub nearest the junction is spaced from it by an odd multiple of a quarter wavelength of the microwave EM radiation transmitted by the microstrip. The subsequent stubs are separated from one another by half the wavelength. Using more than one stub increase the effectiveness of the filter in preventing microwave EM radiation from escaping into the RF pathway 212, 214.

The isolating circuit 200 comprises a waveguide isolator 202 and a coaxial isolator 204 (also referred to as a DC break) connected in series on the microwave signal pathway 210 between the microwave signal generator 220 and second input 205. The waveguide isolator 202 and coaxial isolator 204 are effectively capacitors acting as high pass filters. They permit microwave EM radiation from the microwave signal generator 220 to pass to the combining circuit 206, but prevent RF EM radiation from escaping back out of the second input 205 of the combining circuit 206 into the microwave signal generator 220.

In this embodiment, the microwave channel also include a grounded stub 221 having a length equal to an odd multiple of a quarter wavelength of the microwave EM radiation transmitted by the microstrip to short out any residual RF EM radiation that does escape through the waveguide isolator and coaxial isolator, whilst keeping the microwave transmission losses to a minimum.

The waveguide isolator 202 includes an input port 230 arranged to couple microwave EM radiation from the microwave signal generator 220 into the waveguide cavity of the waveguide isolator 202, and an output port 232 arranged to couple microwave EM radiation from the waveguide cavity to the coaxial isolator 204. The waveguide isolator 202 thus causes both the signal and ground conductors of the microwave signal pathway 210 directed into the coaxial isolator 204 (and hence into the combining circuit 206) to be floating.

An insulating sleeve 229 is provided at the output port 228 of the housing to prevent a current path for connecting the grounded casing of the housing with the floating components connected to the output port 228. The output port 228 may comprises a Type N screw thread or a quick release connector, e.g. to allow different probes to be attached to the housing.

The waveguide isolator 202 is capable of transferring the microwave EM radiation into the combining circuit 206 and on to the probe with low losses while providing sufficient levels of patient protection. The waveguide isolator 202 itself may consist of a cylindrical waveguide arrangement formed by telescoping together a first section with a cooperating second section. Each section may have a connector for coupling microwave EM radiation into or out of the waveguide. For example, each connecter may comprise a Type N receptacle plug from which an E-field probe extends into the waveguide cavity to couple microwave energy to or from the cavity.

The inner surfaces of the sections are separated from each other by a layer of dielectric material (in this embodiment an insulation film, e.g. made of Kapton). The outer surfaces are separated by rigid insulating ring, e.g. made of Delrin® plastic or polyvinylchloride (PVC). The waveguide isolator 202 thus provides a series capacitor on both the signal transmission path (i.e. between inner conductors) and between the ground (i.e. outer) conductors.

A cylindrical waveguide is preferred in order to meet the stringent requirements for the creepage distance and air clearances set by the International Electrotechnical Commission (IEC) standard 60601-1. In the present invention, the power and voltage levels may require the creepage distance to be at least 21 mm and the air clearance to be at least 12 mm. Other aspects of the geometry of the waveguide are determined as follows.

The distance between the end walls (which are grounded) and the centre of the E-field probe is preferably a quarter wavelength at the frequency of the microwave radiation, i.e. to transform a short circuit condition (no E-field) to an open circuit (maximum E-field). The distance between the centres of the two E-field probes is preferably a multiple of a half a wavelength at the frequency of the microwave radiation, whereby the impedances will be identical.

The dominant mode of signal propagation (which exhibits the lowest insertion loss) through a cylindrical waveguide is the TE11 mode. The diameter D of the waveguide required to enable the signal to propagate is given by $$D = \frac{1.8412c}{\pi f \sqrt{\mu_r \epsilon_r}}$$

where c is the speed of light in a vacuum, f is the frequency of operation, $\mu_r$ is the relative permeability for a magnetic loading material (magnetic loading factor), $\epsilon_r$ is the relative permittivity for an electric loading material (dielectric loading factor), and the factor 1.8412 comes from the solution of the Bessel function for a cylindrical waveguide that supports the dominant $TE_{11}$ mode of propagation and the calculation for the cut-off frequency for lowest insertion loss at the frequency of operation.

For example, if the structure is not loaded (as is preferred to achieve the lowest insertion loss), the diameter D for the dominant mode to propagate at 5.8 GHz is greater than 30.3 mm. The actual diameter used may be chosen to take into account or exclude modes that may propagate at larger diameters. In one embodiment, the diameter is 40.3 mm.

A cylindrical waveguide is ideal for achieving the higher levels of protection noted above. However, care is needed to ensure that there is not too much capacitance across the isolated grounds (outer conductors), which may increase the amount of RF energy coupled between the RF signal path and the isolated ground, thus increasing the chances of electric shock and burns to the patient.

There are several sources of reflections between the detector and the distal end of the cable in the arrangement shown in FIG. 2. These include:
the output connector from the amplifier,
the waveguide isolator 202,
the capacitive structure (DC break) 204,
the signal combiner (diplexer) 203,
connection structures (e.g. coaxial joints) 230, 232, etc. between the above components,
the connection 228 between the cable and the output of the generator,
the connection at the proximal end of the electrosurgical tool, and
imperfections in the coaxial cable.

In order to reduce the effect of reflections, and minimise the signal that needs to be removed from the measurement, these individual contributions need to be reduced or minimised if possible.

The output connector from the amplifier may use a standard connector, such as an N-type connector. An N-type connector has a typical VSWR of 1.1, which corresponds to a return loss of about 26 dB. This cannot readily be controlled, and might be expected to vary over the range from infinite return loss (perfect) to 20 dB.

The waveguide isolator 202 can be expected to have a return loss close to 20 dB. This can be adjusted by the use of tuning screws at the input and/or output, but is unlikely to be improved much further. This is partly due to the limits of measurement uncertainty and because the input and output connectors need to be undone and re-connected after adjusting and measuring the return loss on the test equipment.

The DC break 204 may exhibit a return loss in the region of 12 dB to 14 dB. The present invention seeks to reduce this loss, through the use of tuning screws 231 in the waveguide isolator 202 and/or adjustable reactance on the RF channel. Alternatively, the loss can be reduced by providing the DC break as part of the waveguide isolator (see FIGS. 3 and 4).

The diplexer has a return loss close to 20 dB. This is unlikely to be reliably improved for similar reasons to those given above.

The connection structures may include conventional N-type coaxial elbow joints between the above components. Such elbow joints are expected to have a typical VSWR of 1.2, so a return loss close to 21 dB, each.

The connector at the output from the generator may be a Q-N connector, which is typically specified to have a return loss of 25 dB.

The connector at the proximal end of the tool may be a Q-MA connector, which is typically specified to have a return loss of 25 dB.

Slight damage to the cables, e.g. arising from kinking or denting, may result in a return loss of 20 dB from part way down the cable. Care in handling the cable can assist in reducing this loss.

Table 1 shows the combined effect of the typical values of return loss arising from the reflections discussed above.

TABLE 1

Combined effect of return losses

| | Return loss (dB) | Power reflection coefficient | Voltage reflection coefficient | VSWR |
|---|---|---|---|---|
| Connector | 26 | 0.0025 | 0.050 | 1.11 |
| UHF Isolator | 20 | 0.0100 | 0.100 | 1.22 |
| Elbow | 21 | 0.0079 | 0.089 | 1.20 |
| DC break | 12 | 0.0631 | 0.251 | 1.67 |
| Elbow | 21 | 0.0079 | 0.089 | 1.20 |
| Diplexer | 20 | 0.0100 | 0.100 | 1.22 |
| Q-N | 25 | 0.0032 | 0.056 | 1.12 |
| Q-MA | 25 | 0.0032 | 0.056 | 1.12 |
| 'RMS' | 9.673 | 0.1078 | 0.328 | 1.98 |
| Max | 3.565 | 0.4401 | 0.663 | 4.94 |

Table 1 also shows the associated power reflection coefficient, voltage reflection coefficient and VSWR. Because the phase of each reflection is not known—and may vary from assembly to assembly—the total return loss is uncertain. However it is possible to calculate a 'RMS' value and a worst (or Maximum) value. The 'RMS' value is calculated by adding the power reflection coefficients. If there are several reflections, and the total is still small compared to unity, this gives a good estimate of the likely value. The maximum value is calculated using the product of the VSWRs. This is exact, and the VSWR cannot exceed this value, but will rarely reach it.

It can be seen that the power reflection coefficient of the DC break is over 60% of the final total, so that reducing this could reduce the 'RMS' value by over 50%, resulting in an improvement in the return loss from −9.7 dB to −12.6 dB, as shown in Table 2.

TABLE 2

Combination of reflections - improved DC break

| | Return loss (dB) | Power reflection coefficient | Voltage reflection coefficient | VSWR |
|---|---|---|---|---|
| Connector | 26 | 0.0025 | 0.050 | 1.11 |
| UHF | 20 | 0.0100 | 0.100 | 1.22 |

TABLE 2-continued

Combination of reflections - improved DC break

| | Return loss (dB) | Power reflection coefficient | Voltage reflection coefficient | VSWR |
|---|---|---|---|---|
| Isolator Elbow | 21 | 0.0079 | 0.089 | 1.20 |
| DC break | 20 | 0.0100 | 0.100 | 1.22 |
| Elbow | 21 | 0.0079 | 0.089 | 1.20 |
| Diplexer | 20 | 0.0100 | 0.100 | 1.22 |
| Q-N | 25 | 0.0032 | 0.056 | 1.12 |
| Q-MA | 25 | 0.0032 | 0.056 | 1.12 |
| 'RMS' | 12.618 | 0.0547 | 0.234 | 1.61 |
| Max | 4.935 | 0.3210 | 0.567 | 3.61 |

To achieve the improvement shown in Table 2, the embodiment shown in FIG. 2 has a set of tuning stubs 231 (three stubs in this example) incorporated into the waveguide isolator 202. In addition, to permit the apparatus to be used with different lengths of coaxial cable (which present different capacitances to the line up of components), the RF channel may have an adjustable reactance 217. The adjustable reactance may comprise switched or electronically tunable capacitors or inductors that are controlled by a control signal $C_1$ from the microprocessor.

Figure 3:
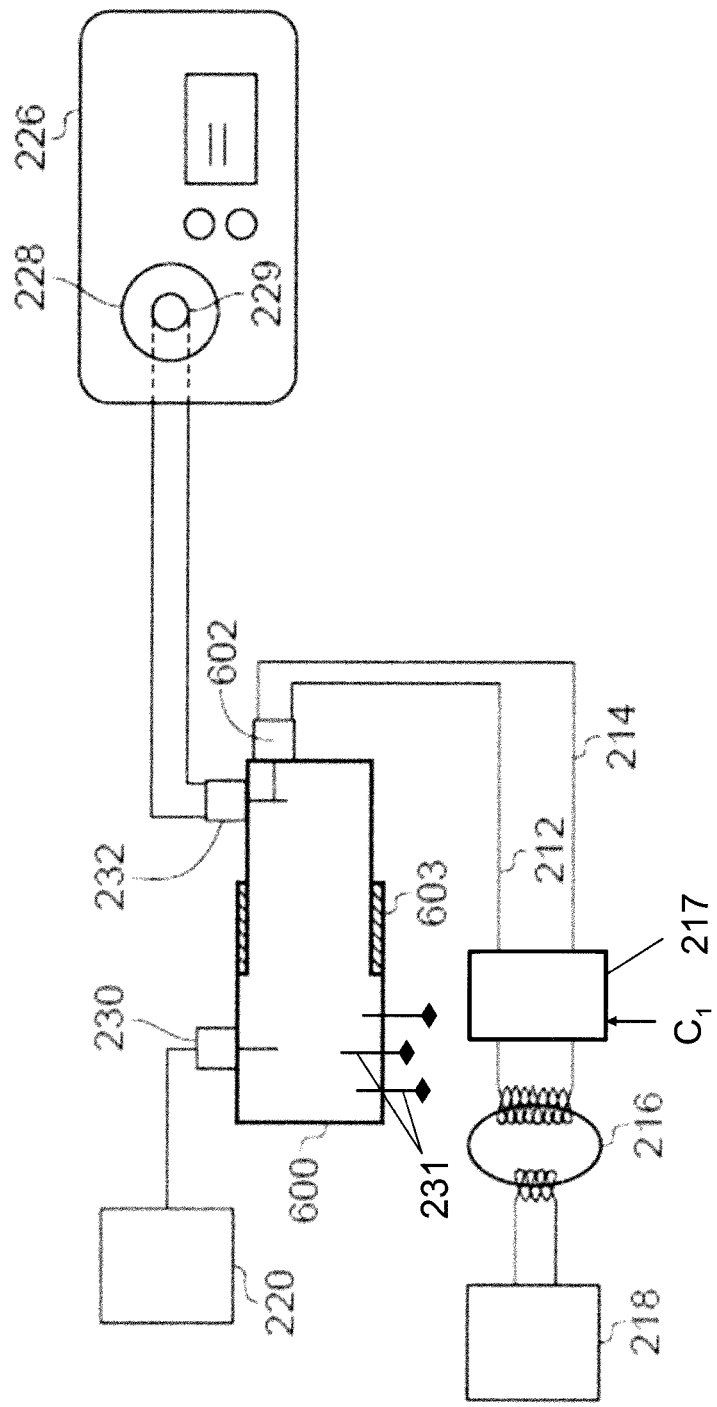
FIG. 3 is a schematic diagram of an isolating circuit having only a waveguide isolator that is another embodiment of the invention.

FIG. 3 is a schematic diagram showing another embodiment of an isolating circuit for an electrosurgical apparatus. Features in common with the embodiment of FIG. 2 are given the same reference numbers and are not described again. In this embodiment, the isolating circuit comprises a waveguide isolator 600 whose insulating gap is configured to provide the necessary level of DC isolation whilst also having an capacitive reactance that is high enough at the frequency of the RF energy to prevent coupling of RF energy across the insulating gap and low enough at the frequency of the microwave energy to prevent leakage of the microwave energy at the gap. The configuration of the gap is explained in detail with reference to FIG. 4. The gap may be 0.6 mm or more, e.g. 0.75 mm. This configuration means that the coaxial isolator used in the embodiment of FIG. 2 is not needed.

In addition, in this embodiment the combining circuit is integrated with the waveguide isolator 600. The signal conductor 212 and ground conductor 214 carrying the RF signal are connected to a coaxial RF connector 602 (RF feed), which introduces the RF signal into the waveguide isolator 600, from where it is conveyed out from the output port 232 towards the probe. The isolating gap 603 is arranged to prevent the RF signal from coupling back into the input port 230. Microwave energy is prevented from coupling into the RF connector 602 by careful placement of the inner conductive rod within the waveguide isolator, as explained below. Combining the RF and microwave energy in the waveguide isolator obviates the need of a separate combining circuit, which reduces the number of components required for the isolating circuit and enables it to be provided as a more compact unit.

A tuning unit is incorporated into the waveguide isolator 600 in order to reduce the return loss of the line up of components, as discussed below. In this embodiment, the tuning unit comprises three stubs 231 that can be adjustably inserted, e.g. screwed, into the body of the cavity.

In addition, similarly to FIG. 2, the RF channel has an adjustable reactance 217 that is operable under the control of control signal $C_1$ from the microprocessor to accommodate (e.g. compensate for) changes in capacitance arising from different lengths of cable used with the generator. The adjustable reactance 217 may comprise one or more of switched or electronically tunable capacitors or inductors connected in shunt or series with the RF channel. The location of the adjustable reactance before the isolator 600 is preferred, since if it was after the isolator it may be necessary to build additional microwave chokes to prevent the RF capacitance from changing the microwave impedance.

Figure 4:
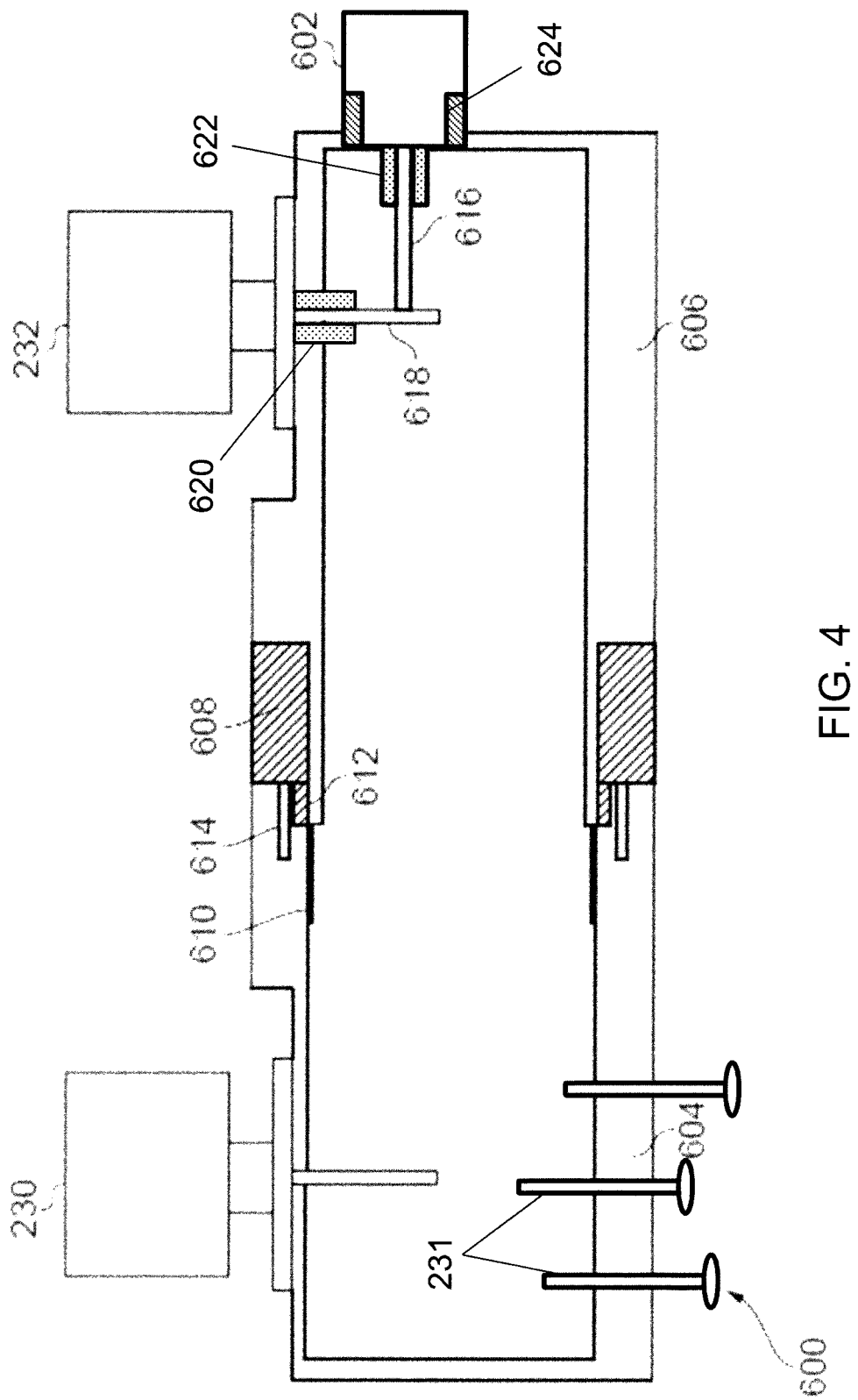
FIG. 4 is a cross-sectional side view of an adapted waveguide isolator suitable for use in the isolating circuit of FIG. 3.

FIG. 4 shows a cross-sectional side view of the adapted waveguide isolator 600 used in the isolating circuit of FIG. 3. The waveguide isolator 600 has a cylindrical body made up of two mating parts. In this embodiment, an input section 604 is a female component having an opening for receiving an output section 606, which has a cooperating male component. An input port 230 and an output port 232 are mounted on the input section 604 and output section 606 respectively. In this embodiment, the tuning screws 231 are in the input section 604.

In practice the tuning section will located along the waveguide from the input connector/probe. FIG. 4 shows an arrangement where the tuning screws are opposite the input probe, but it may be preferred to have them in a short section of waveguide that has no other components in it. In practice, if other components are 30 mm or more away from the tuning screws along the length of the waveguide, any potential interaction between those components and the tuning screws can be avoided.

The tuning screws may be provided in the output section of the waveguide. However, in the present embodiment the output section has a diameter selected to permit the $TM_{01}$ mode to propagate. In this case it is preferable to avoid locating the tuning screws in the output section to ensure that this mode is not excited accidentally.

The DC gap, which insulates the input section 604 from the output section 606 comprises a number of component parts. The component parts all have rotational symmetry around the axis of the cylindrical body. A first component part is a primary insulating ring 608, e.g. made of rigid material such as Delrin® plastic or polyvinylchloride (PVC), which surrounds the male component of the output section 606 and separates (and electrically isolates) the outer surfaces of the input section 604 and output section 606.

The axial length of the insulating ring 608 is shorter than the male component of the output section 606, so that a length of the male component extends beyond the distal end of the insulating ring 608. This section of the male component overlaps with the distal end of the female component of the input section 604. A second component part of the DC gap is a secondary insulating ring 612 (which may be formed in one piece with the primary insulating ring 608) which provide a radial insulation between the distal ends of the male and female components.

A third component part of the DC gap is an insulating film 610 (e.g. one or more layers of Kapton® tape) which cover the inside surface of the input section 604 for an axial length beyond the distal end of the output section 606. The insulating film can isolate the input section from any fringing fields at the distal end of the output section 606.

A fourth component part of the DC gap is an air-filled microwave choke 614, which is a narrow annular channel in the distal end of the input section 604. The presence of the microwave choke 614 lowers the capacitive reactance at the frequency of the microwave energy, which prevents leakage (e.g. radiation) of the microwave energy at the DC gap.

The increased complexity of the DC gap configuration in this embodiment increases the capacitive reactance at the frequency of the RF energy by widening the 'average' gap between the input and output sections. Meanwhile the presence of the microwave choke 614 makes use of resonant effects to ensure that the capacitive reactance at the frequency of the microwave energy is low enough to avoidance leakage of microwave energy from the gap.

In this embodiment, the waveguide isolator also acts as the combining circuit. The RF connector 602 has an inner conductive rod 616 that projects into the waveguide isolator, where it meets the inner conductor 618 of the coaxial output probe (output port 232) at a point spaced from the end of the inner conductor 618. The position of the inner conductive rod is selected to lie substantially parallel to the equipotentials of the microwave energy in the waveguide isolator (i.e. it is, on average, perpendicular to the field lines in the isolator) so that it does not couple any significant microwave power. This position can be determined by known simulation techniques. Given that the conductive rod 616 is not driven by the microwave energy and does not carry any microwave current, its thickness can be selected without negative impact. A simple wire similar to the inner conductor 618 is suitable.

Because the clearances are large the voltage stand-off is expected to be high. Accordingly, the dielectric material (e.g. PTFE sleeves 620, 622) that surrounding the inner conductor 618 and conductive rod 616 respectively as they pass through the wall of the isolator 600 is arranged to extend some distance into the cavity. This arrangement may increase the distance for tracking across the point where the probe comes into the cavity (RF feed and microwave feed), and is thus an effective way of increasing the breakdown voltage.

In addition, a microwave choke 624 may be provided on the outside of the RF feed to reduce any leakage of microwave energy. This could either be an add-on or built in. The microwave choke 624 is depicted in this embodiment as a cylindrical element in the outer wall of the RF feed. However a radial choke may work equally well.

The stubs 231 in the waveguide isolator 600 can be adjusted when the device is under test, to reduce the total reflection from all the components in the line up to below −20 dB. The effect of this is shown below in Table 3. The 'RMS' return loss is −17.2 dB, and the worst case would be −11.8 dB.

TABLE 3

Combination of reflections - integrated isolator

|  | Return loss (dB) | Power reflection coefficient | Voltage reflection coefficient | VSWR |
| --- | --- | --- | --- | --- |
| Connector | 26 | 0.0025 | 0.050 | 1.11 |
| Integrated isolator | 20 | 0.0100 | 0.100 | 1.22 |
| Q-N | 25 | 0.0032 | 0.056 | 1.12 |
| Q-MA | 25 | 0.0032 | 0.056 | 1.12 |
| 'RMS' | 17.25 | 0.0188 | 0.137 | 1.32 |
| Max | 11.7954 | 0.0661 | 0.257 | 1.69 |

If the tuner is used in-situ, while the return loss is monitored using the backward power detector, it should be possible to reduce the combined effect of coupler breakthrough and return loss for all connected components to below 20 dB, provided that the assembly was terminated in a good load, i.e. a load with a return loss significantly better than 30 dB. This will leave only the unwanted reflections from the QN and QMA connectors and any imperfections in the cables. The typical remaining VSWR and return loss from these components is shown in Table 4.

TABLE 4

Combination of reflections - tuned in-situ

| | Return loss (dB) | Power reflection coefficient | Voltage reflection coefficient | VSWR |
|---|---|---|---|---|
| Q-N | 25 | 0.0032 | 0.056 | 1.12 |
| Q-MA | 25 | 0.0032 | 0.056 | 1.12 |
| 'RMS' | 21.9897 | 0.0063 | 0.080 | 1.17 |
| Max | 19.00682 | 0.0126 | 0.112 | 1.25 |

This correction would be effective over a bandwidth determined by the delay distance between the significant reflections, including the tuner, and also the coupler breakthrough. If the load used were, for instance, a lossy cable on the far side of the Q-MA connector, the delay distance between coupler breakthrough and the reflection at the Q-MA connector would be about 2 m (taking into account a typical length of the generator line up, the cable, and the dielectric constant inside the cable). For the interference between reflections this far apart to go through one complete cycle, the frequency would need to change by 750 MHz. At $\frac{1}{12}$ of this bandwidth the cancellation would be 6 dB, with the cancellation increasing 6 dB for every halving of bandwidth. For 15 MHz bandwidth cancellation of 18 dB should be achieved. As the original combined return loss for these two components is expected to be no more than 17 dB this should be reduced below 35 dB over 15 MHz bandwidth.

For example, if the return loss to be measured is in the region of 14 dB to 24 dB, and the total unwanted signal can be kept below 35 dB this will result in uncertainties of about 14 dB+/−0.8 dB and about 24 dB+/−2.5 dB.

As discussed above with respect to FIG. 1, the microwave channel includes a power amplifier 412. The following discussions describes improvements to the power amplifier and associated components which may form an independent aspect of the invention described herein.

There are several areas where the performance and behaviour of the power amplifier 412 and associated forward and reverse detectors 414, 418 may be optimised for use in the electrosurgical generator described above:
  higher power output;
  sensitivity of the forward and reverse detectors;
  reduction of generator noise in the monitoring signals output from the power amplifier.

In order to get higher power it is necessary either to use more amplifier chips or to increase the power of each chip. In the known arrangement shown in FIG. 1, the power amplifier 412 comprises one initial transistor driving four transistors in parallel in the power output stage, which give about 25 W each. If this configuration is maintained, it would be desirable to generate more than 40 W at each of these transistors. Increasing the number of transistors would require a change in the splitter design and the use of more board space for the extra component(s).

It is desirable for the frequency of the microwave energy to be 5.8 GHz. At this frequency, it is desirable to be able to deliver 120 W at the output of the generator with spare performance in hand for de-rating due to temperature variation. It is necessary to make a careful selection of transistor based on gain and saturated power output, as shown by the following analysis.

Table 5 below shows some performance parameters of some microwave power transistors suitable for use at 5.8 GHz.

TABLE 5

Parameters of Some GaAs Transistors

| | | Gain dB 1 dB | dBm 1 dB | Gain dB | dBm 3 dB | Gain dB | dBm | | |
|---|---|---|---|---|---|---|---|---|---|
| Toshiba | TIM5359-60SL | 8 | 47 | | | | | | |
| Integra | IGN5259M80 | | | | | 12.8 | 50 | Not CW | 300 ms |
| | | | | | | 12.8 | 47 | CW | |
| Mitsubishi | MGFC50G5867 | | | 10 | 50 | | | | |
| Mitsubishi | MGFC47G5867 | | | 10 | 47 | | | | |

A simple spreadsheet model was constructed to determine which transistors could be used. The required output power was set at 120 W. For the parameters in Table 6 the model gives the results shown in Table 7.

TABLE 6

Constants for Simple Power Output Stages

| Transistor Power | 75 | W |
|---|---|---|
| Transistor Gain | 10 | dB |
| Splitter | −3.5 | dB |
| Combiner | 2.5 | dB |
| Circulator | −0.5 | dB |
| DC break | −0.5 | dB |

TABLE 7

Power Through Simple Combiner Circuit and Output Stages

| Gain out of stage (dB) | Power out of stage | | |
|---|---|---|---|
| | (dBm) | (W) | |
| 0 | 35.75061 | 3.758904 | Required input power |
| 10 | 45.75061 | 37.58904 | Power out of first transistor |
| 6.5 | 42.25061 | 16.79041 | Power after 2-way split |
| 3 | 38.75061 | 7.5 | Power after second 2-way split |
| 13 | 48.75061 | 75 | Power from one transistor |
| 15.5 | 51.25061 | 133.371 | Power after first combiner |
| 18 | 53.75061 | 237.1708 | Power after second combiner |
| 17.5 | 53.25061 | 211.3787 | Power after circulator |
| 17 | 52.75061 | 188.3915 | Power after DC break |

This model shows that using five transistors, with a single one as the preamplifier followed by four in parallel, for an input power of about 3.75 W an output power of about 188 W might be expected. This is less gain than the 20 dB expected from the amplifiers, because 0.5 dB loss has been allowed for each of two two-way splitters, each of two two-way combiners, and for the circulator and output DC break, making a total of 3 dB loss.

A transistor power of 75 W and gain of 10 dB has been used, which may for example corresponds to a de-rated Mitsubishi MGFC50G5867. This allows just over 1 dB headroom for thermal degradation of saturated output power. Even with this de-rating, the modelled output power of 188 W is nearly 2 dB above the target of 120 W. Although four transistors with 50 W output power can be combined to give 125 W output, there is only 0.2 dB headroom for thermal de-rating (or for other non-optimal performance). This is too low and would probably lead to power stability problems at high temperatures or after long use, similar to those seen with the present amplifier.

This analysis demonstrates how extra power can be achieved without requiring a new board layout or the expense of additional transistor components.

Turning now to the forward and reverse detector configuration, the improvements proposed herein seek to address three issues:

(1) poor directivity of the couplers;

(2) significant attenuation of the reflected signal from the probe by the cables. This attenuation causes the signal to be comparable with other small signals reflected from connectors and other components in the transmission line, and also with breakthrough of the forward signal through the circulator. There may also be breakthrough from the reflection from the termination of the reverse signal line, because there is poor coupler directivity. This makes it very difficult to accurately measure the signal from the probe using a simple power detector.

(3) contamination of the forward detector signal by reflections from the circulator and by breakthrough of the reverse signal through the circulator, both of which may be only 15 dB below the forward signal. This is exacerbated by the poor directivity of the detector coupler.

The forward detector performance can be improved in the following ways.

Firstly, the directivity of the forward detector coupler can be improved to 20 dB or more through appropriate modelling and design, i.e. taking into account the substrate, impedance, coupling factor and geometry. It is undesirable to try to tune the coupler after assembly to achieve a desired diode power, since this often has a bad effect on directivity. The performance of the reverse detector can be improved in a similar way.

Secondly, the isolation and return loss of the circulator may be improved to 20 dB or better. This could be done by using a 4-port circulator. Doing this would also improve the reverse detector performance.

A significant improvement can be gained by using a quadrature mixer instead of the reverse detector (which is a square law detector), so that the vector sum of the unwanted signals can be measured and then subtracted from the vector sum of the total signal including the reflection from the tip. It is possible to achieve 20 dB cancellation of unwanted signals using this method. A quadrature mixer requires a reference signal that is coherent with the signal to be measured, i.e. one that is generated using the same clock signal. The reference signal (100 mW) could be taken (coupled) from before or after the power amplification stage.

The improvement provided by a quadrature mixer over a square law detector is demonstrated by the following analysis.

A square law detector gives an output signal proportional to the square of the voltage at the input. This would contain multiple of frequencies generated by the squaring process, but these are filtered out by a low pass filter so that only a slowly varying signal is output, i.e. at a frequency much less than the microwave frequency. If there are multiple signals arriving at the detector at once, the output is the square of the sum of the voltages from all the signals.

$$V_{SUM} = \sum_n v_n$$
$$= \sum_n \text{real}[a_n \exp(j(\omega_n t + \phi_n))]$$
$$= \text{real}\left[\sum_n a_n \exp(j(\omega_n t + \phi_n))\right]$$
$$= \sum_n a_n [\exp(j(\omega_n t + \phi_n)) + \exp(-j(\omega_n t + \phi_n))]$$

$$V_{SUM}^2 = \left\{\sum_n v_n\right\}^2$$
$$= \left\{\sum_n a_n [\exp(j(\omega_n t + \phi_n)) + \exp(-j(\omega_n t + \phi_n))]\right\}^2$$
$$= \sum_m \sum_n a_m a_n \begin{bmatrix} \exp(j((\omega_m + \omega_n)t + \phi_m + \phi_n)) + \\ \exp(j((\omega_m - \omega_n)t + \phi_m - \phi_n)) + \\ \exp(-j((\omega_m - \omega_n)t + \phi_m + \phi_n)) + \\ \exp(-j((\omega_m - \omega_n)t + \phi_m - \phi_n)) \end{bmatrix}$$

All of these components have a frequency $(\omega_m + \omega_n)$ or $|\omega_m - \omega_n|$. If m=n then $|\omega_m - \omega_n| = 0$ and this is a DC term, and can be selected using a low-pass filter.

If the signals are all at different frequencies, the resulting DC signal is $$V_{DC}^2 = 2\sum_n a_n^2.$$

If the signals are at the same frequency, then the square of the sum of the voltages is $$V_{SUM}^2 = \left\{\sum_n v_n\right\}^2$$
$$= \left\{\sum_n a_n [\exp(j(\omega t + \phi_n)) + \exp(-j(\omega t + \phi_n))]\right\}^2$$
$$= \sum_m \sum_n a_m a_n \begin{bmatrix} \exp(j(2\omega t + \phi_m + \phi_n)) + \\ \exp(j(\phi_m - \phi_n)) + \\ \exp(-j(2\omega t + \phi_m + \phi_n)) + \\ \exp(-j(\phi_m - \phi_n)) \end{bmatrix}$$

The DC component of this is $$V_{DC}^2 = \sum_m \sum_n a_m a_n [\exp(j(\phi_m - \phi_n)) + \exp(-j(\phi_m - \phi_n))]$$
$$= 2\sum_m \sum_n a_m a_n \cos(\phi_m - \phi_n)$$

The complication that comes with this is that the cosine can be positive or negative, depending on the difference of the two phases in the brackets, and in some cases the sum can be zero.

This means that with one signal, or with multiple signals at different frequencies, we can measure the total power with a square law detector, but with two or more signals at the same frequency we may sometimes measure no power, and will usually not measure the total power.

If a measurement is made with one less signal (i.e. when the signal we are looking for is switched off), and another after the signal is added (i.e. switched on again), the difference will be $$V_{DC}^2 = 2\sum_N \sum_N a_m a_n \cos(\phi_m - \phi_n) - 2\sum_{N-1}\sum_{N-1} a_m a_n \cos(\phi_m - \phi_n)$$
$$= 2a_N \sum_{N-1} \{a_N \cos(\phi_N - \phi_n)\} + a_N^2$$
$$= a_N \left(2\sum_{N-1} \{a_n \cos(\phi_N - \phi_n)\} + a_N\right)$$

So the difference is not just equal to the power in the extra signal, but involves the sum of lots of other terms, that may be positive or negative.

The power of one signal cannot be determined if other signals of the same frequency are also present at the square-law detector, unless the phases of all the extra terms can be varied independently, or the phase of the signal to be determined can be varied independently so that the cosine terms in the sum can be eliminated. This could be done by, for instance making two measurements in which the phase of the signal to be measured varied by 180 degrees, but the phases of all the other signals were unchanged. The sums in the two difference signals would then cancel each other if added together, but the wanted signal would add.

$$\left[2a_N \sum_{N-1}\{a_n \cos(\phi_N - \phi_n)\} + a_N^2\right] + \left[2a_N \sum_{N-1}\{-a_N \cos(\phi_N - \phi_n)\} + a_N^2\right] = 2a_N^2$$

It is not clear how the phase of the desired signal could be varied without changing the phases of the unwanted signals, or how the phases of the other signals could be varied without changing the phase of the desired signal. If this cannot be done then a square-law detector cannot measure the power of the desired signal when there are other unwanted signals present at the same frequency (i.e. reflections and breakthrough).

The quadrature detector differs significantly from the square-law detector, in three ways:
- it requires two inputs, the signal to be measured, and a reference signal.
- it has two outputs, which are out of phase by 90 degrees (one quarter of a cycle at the frequency of the reference signal).
- each of the output signals is proportional to the total input voltage, not to the power.

The two output channels are commonly referred to as "I" and "Q", "cosine" and "sine" or "in-phase" and "quadrature". They are proportional to total input voltage, and to the cosine and sine of the phase of the total signal.

The two signals are $I = A|V_{TOT}|\cos(\varphi_{TOT} - \varphi_{REF})$ and $Q = A|V_{TOT}|\sin(\varphi_{TOT} - \varphi_{REF})$.

It is then possible to determine $A|V_{TOT}|$ and $(\varphi_{TOT} - \varphi_{REF})$ from the I and Q signals, where A is the voltage gain of the mixer (usually specified as conversion loss in dB).

$$V_{TOT} = |V_{TOT}|\exp(j\phi_{TOT}) = \sum_n |V_n|\exp(j\phi_n)$$

If the signal to be measured is not present (but all the interfering signals are still there) then $$V_{NOT} = |V_{NOT}|\exp(j\phi_{NOT}) = \sum_{N-1} |V_n|\exp(j\phi_n) = V_{TOT} - |V_N|\exp(j\phi_N)$$

The desired signal can be identified by the difference between the two measurements.

$$AV_N = A(V_{TOT} - V_{NOT}) =$$
$$A\left(\sum_N |V_n|\exp(j\phi_n) - \sum_{N-1} |V_n|\exp(j\phi_n)\right) = A|V_N|\exp(j\phi_N)$$

A quadrature mixer can be bought as a chip or IC, e.g. Hittite HMC525.

The quadrature detector can use a reference signal at nominally the same frequency as the signal to be detected, or it can use a reference signal with a different frequency. Any difference must be less than the IF bandwidth of the detector.

In the first case the detected signal is down-converted to (a small band around) DC. In the second case the signal is down-converted to an intermediate frequency (IF). It can then be subsequently down-converted to DC in two secondary mixers (one for each channel).

In order to preserve the (required) phase information in the down-converted signal, it is necessary that all reference signals are derived from the signal frequency reference. For the final result to be at DC the two reference frequencies must add up to (or differ by) exactly the signal frequency reference.

Figure 5B:
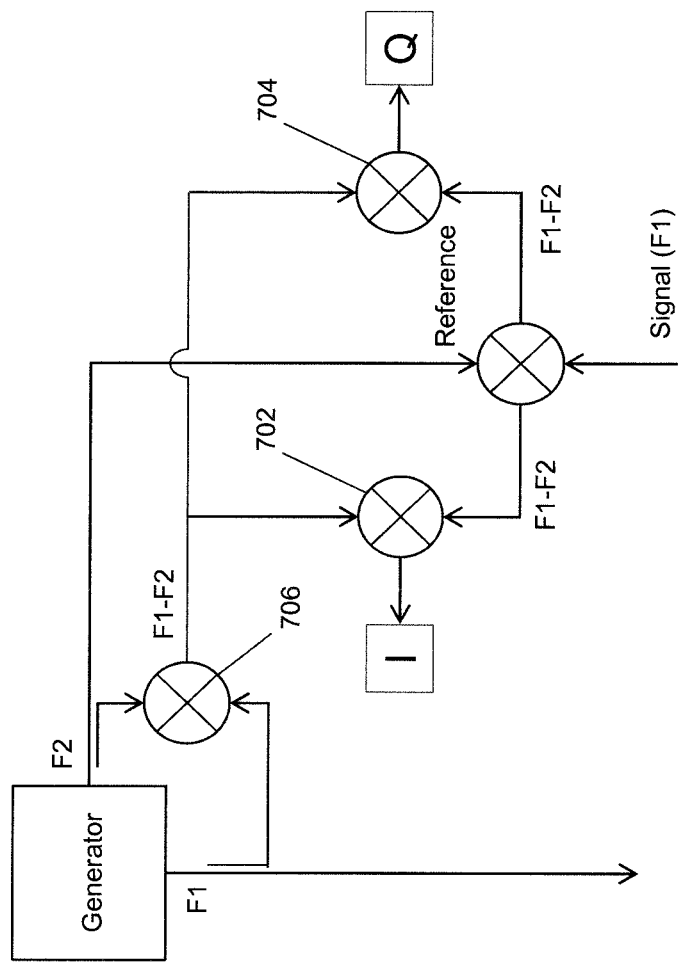
FIGS. 5A and 5B are schematic diagrams of quadrature mixer that may be used in an electrosurgical apparatus of the invention.
Figure 5A:
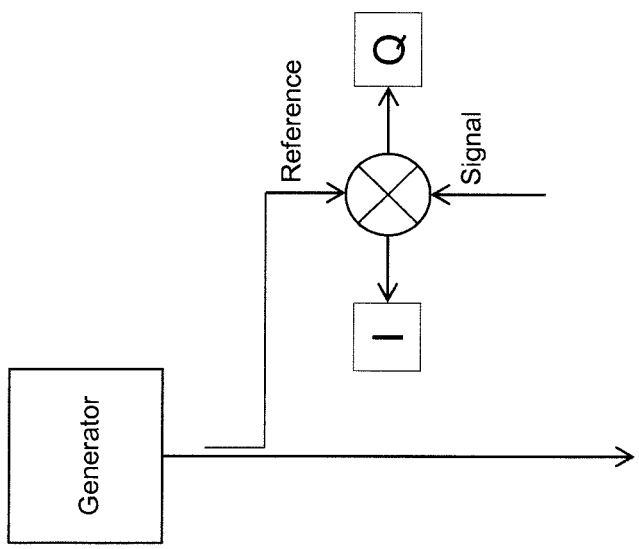

FIG. 5A shows a simplified layout of a quadrature mixer with direct down-conversion to baseband (DC). The circuit does not show any filters, attenuators or phase shifters that may be used in various places.

FIG. 5B shows a more complicated version where the initial down-conversion is to an intermediate frequency. This is most often done when it is necessary to amplify the signal while it is still at a frequency where low-frequency noise is not a problem, but amplifiers and filters are easier to build. It might also be used so that the reference signal and IF could be connected to another part of the board without there being interference (feedback or crosstalk) problems—neither of them are at the frequency of the main signal.

The internal layout is designed so that the signal is equally divided between two internal mixers 702, 704, with the same path length for both parts, but the respective reference paths to the internal mixers 702, 704 from intermediate mixer 706 have a quarter wave difference. This path difference results in the output signals being in quadrature—one of them is compared to a cosine voltage at the reference frequency, and the other to a sine voltage at the reference frequency.

Turning now to the idea of reducing noise on the output signal, there are two likely sources of the noise.

Firstly, the ground of the amplifier is not at chassis ground because of the high current required to drive the amplifier power stage, which results in a voltage drop between the earth of the power supply and that of the amplifier, even when quite thick wires are used.

Secondly, if the power supplies in the generator are pulsed, they create a lot of noise which is coupled to the power amplifier leads and tracks on the generator board where the monitoring signals are digitised. Much of the noise is at frequencies comparable to or higher than the sampling frequency. If high frequency noise is digitised at low sample rates then it is aliased and increases the noise level at low frequencies in the digitised signal.

The noise could be reduced in the following ways.

Firstly, increased noise due to aliasing can be eliminated by properly matching the analogue filter bandwidth to the sampling frequency according to the Nyquist criterion, i.e. the analogue filter bandwidth (top frequency of a low pass filter) before the sampling takes place should be half the digital sampling frequency. If it is required to vary the sampling frequency then the filters should be changed, or multiple filters incorporated so that the correct bandwidth can be selected as required.

Secondly, it may be possible to reduce the noise in the measured signals by incorporating a digital processor in the power amplifier, and digitising all the measured signals before they are output from the amplifier module. If a digital processor were to be incorporated in the power amplifier module then it could be used for other power amplifier control functions.

The invention claimed is:

1. An electrosurgical apparatus for resection of a biological tissue, the apparatus comprising:
   a radiofrequency (RF) signal generator for generating RF electromagnet (EM) radiation having a first frequency;
   a microwave signal generator for generating microwave EM radiation having a second frequency that is higher than the first frequency;
   a probe arranged to deliver the RF EM radiation and the microwave EM radiation separately or simultaneously from a distal end thereof; and
   a feed structure for conveying the RF EM radiation and the microwave EM radiation to the probe, the feed structure comprising an RF channel for connecting the probe to the RF signal generator, and a microwave channel for connecting the probe to the microwave signal generator,
   wherein the RF channel and microwave channel comprise physically separate signal pathways from the RF signal generator and microwave signal generator respectively,
   wherein the feed structure includes a combining circuit having a first input connected to the separate signal pathway on the RF channel, a second input connected to the separate signal pathway on the microwave channel, and an output connected to a common signal pathway for conveying the RF EM radiation and the microwave EM radiation separately or simultaneously along a single channel to the probe,
   wherein the microwave channel includes a waveguide isolator connected to isolate the separate signal pathway on the microwave channel from the RF EM radiation,
   wherein the waveguide isolator has an adjustable impedance,
   wherein the combining circuit is integrated with the waveguide isolator,
   wherein the output connected to the common signal pathway includes an output probe mounted on the output section of the waveguide isolator, the output probe having a coupling conductor extending into the waveguide isolator to couple the microwave EM energy therefrom, and
   wherein the first input includes an RF connector mounted on the waveguide isolator, the RF connector having a signal conductor that extends into a waveguide cavity of the waveguide isolator to electrically contact the coupling conductor of the output probe.

2. The electrosurgical apparatus according to claim 1, wherein the waveguide isolator includes a tuning portion that is adjustable to change the impedance of the waveguide isolator.

3. The electrosurgical apparatus according to claim 2, wherein the tuning portion comprises a plurality of tuning stubs that are adjustably insertable into the waveguide isolator.

4. The electrosurgical apparatus according to claim 1,
   wherein the waveguide isolator comprises a conductive input section, a conductive output section which mates with the input section to define the waveguide cavity within a volume enclosed by the input and output sections, and a DC isolation barrier arranged between the input and output sections,
   wherein the output on the common signal pathway includes a signal conductor and a ground conductor, and
   wherein the feed structure includes a capacitive structure between the ground conductor of the output on the common signal pathway and the conductive input section of the waveguide isolator, the capacitive structure being arranged to inhibit coupling of the RF EM energy and leakage of the microwave EM energy.

5. The electrosurgical apparatus according to claim 4, wherein the capacitive structure is provided by the DC isolation barrier and a microwave choke formed on the input section of the waveguide isolator.

6. The electrosurgical apparatus according to claim 5, wherein the input and output sections of the waveguide isolator define a cylindrical body, and wherein the microwave choke comprises an annular channel extending axially from a distal end of the input section of the waveguide isolator.

7. The electrosurgical apparatus according to claim 4, wherein the DC isolation barrier includes a rigid insulating spacer element mounted between the input and output sections of the waveguide isolator.

8. The electrosurgical apparatus according to claim 7, wherein the DC isolation barrier includes an insulating film mounted on a portion of an inner surface of the input section at a junction with the rigid insulating spacer element.

9. The electrosurgical apparatus according to claim 1, wherein a position of the signal conductor extends substantially along an equipotential of a microwave EM field within the waveguide isolator.

10. The electrosurgical apparatus according to claim 1, wherein a proximal portion of the coupling conductor of the output probe that extends into the waveguide isolator is surrounded by an insulating sleeve.

11. The electrosurgical apparatus according to claim 1, wherein a proximal portion of the signal conductor of the RF connector that extends into the waveguide isolator is surrounded by an insulating sleeve.

12. The electrosurgical apparatus according to claim 1 including a microwave choke mounted on the RF connector to prevent the microwave EM energy from leaking out of the waveguide isolator through the signal conductor of the RF connector.

13. The electrosurgical apparatus according to claim 12, wherein the microwave choke is radial or cylindrical.

14. The electrosurgical apparatus according to claim 1, wherein the RF channel includes a controllably adjustable reactance.

15. The electrosurgical apparatus according to claim 14, wherein the adjustable reactance comprises a capacitance or an inductance that is selectably switchable into the RF channel.

16. The electrosurgical apparatus according to claim 14, wherein the adjustable reactance is an electronically tunable capacitance or an electronically tunable inductance.

17. The electrosurgical apparatus according to claim 4, wherein the capacitive structure includes a coaxial isolator connected in series with the waveguide isolator.

18. The electrosurgical apparatus according to claim 1, wherein the combining circuit comprises a microstrip diplexer circuit.

19. The electrosurgical apparatus according to claim 18, wherein the RF channel includes a low pass, band pass, band stop or notch filter connected between the separate signal pathway on the RF channel and the combining circuit, for blocking microwave EM radiation from entering the separate signal pathway on the RF channel.

20. The electrosurgical apparatus according to claim 1 including a controller operable to select an energy delivery profile for the RF EM radiation and the microwave EM radiation.

21. The electrosurgical apparatus according to claim 20 including an RF signal detector for sampling current and voltage on the RF channel and generating therefrom a RF detection signal indicative of the phase difference between the current and voltage, wherein the controller is in communication with the RF signal detector to receive the RF detection signal and is arranged to select the energy delivery profile for the RF EM radiation based on the RF detection signal.

22. The electrosurgical apparatus according to claim 20 including a microwave signal detector for sampling forward and reflected power on the microwave channel and generating therefrom a microwave detection signal indicative of a magnitude and/or phase of microwave power delivered by the probe, wherein the controller is in communication with the microwave signal detector to receive the microwave detection signal and is arranged to select the energy delivery profile for the microwave EM radiation based on the microwave detection signal.

23. The electrosurgical apparatus according to claim 1, wherein the distal end of the probe comprises a bipolar emitting structure comprising a first conductor spatially separated from a second conductor, the first and second conductors being arranged to act:
   as active and return electrodes respectively to convey the RF EM radiation by conduction, and
   as an antenna or impedance transformer to convey the microwave EM radiation by radiation.

24. The electrosurgical apparatus according to claim 1, wherein the first frequency is a stable fixed frequency in the range 10 kHz to 300 MHz and the second frequency is a stable fixed frequency in the range 300 MHz to 100 GHz, the second frequency being at least an order of magnitude higher than the first frequency.

25. An isolating circuit for electrosurgical apparatus for resection of biological tissue, the isolating circuit comprising:

a combining circuit having a first input connectable to receive radiofrequency (RF) electromagnetic (EM) radiation having a first frequency from an RF channel, a second input connectable to receive microwave EM radiation having a second frequency that is higher than the first frequency from a microwave channel, and an output in communication with the first and second inputs for conveying the RF EM radiation and the microwave EM radiation to a common signal pathway, and a waveguide isolator connected to isolate the microwave channel from the RF EM radiation, wherein the waveguide isolator comprises a conductive input section, a conductive output section which mates with the input section to define a waveguide cavity within a volume enclosed by the input and output sections, and a DC isolation barrier arranged between the input and output sections, wherein the output from the combining circuit includes a signal conductor and a ground conductor, wherein the output connected to the common signal pathway includes an output probe mounted on the conductive output section of the waveguide isolator, the output probe having a coupling conductor extending into the waveguide isolator to couple the microwave EM energy therefrom, wherein the first input includes an RF connector mounted on the waveguide isolator, the RF connector having a signal conductor that extends into the waveguide cavity to electrically contact the coupling conductor of the output probe, wherein the isolating circuit comprises a capacitive structure between the ground conductor of the output from the combining circuit and the conductive input section of the waveguide isolator, the capacitive structure being arranged to inhibit coupling of the RF EM energy and leakage of the microwave EM energy, and wherein the waveguide isolator has an adjustable impedance.

26. The isolating circuit according to claim 25, wherein the waveguide isolator includes a tuning portion that is adjustable to change the impedance of the waveguide isolator.

27. The isolating circuit according to claim 26, wherein the tuning unit comprising a plurality of tuning stubs that are adjustably insertable into the waveguide isolator.

28. The isolating circuit according to claim 25, wherein a position of the signal conductor is substantially aligned with an equipotential of the microwave EM energy within the waveguide isolator.

29. The isolating circuit according to claim 25, wherein a proximal portion of the coupling conductor of the output probe that extends into the waveguide isolator is surrounded by an insulating sleeve.

30. The isolating circuit according to claim 25, wherein a proximal portion of the signal conductor of the RF connector that extends into the waveguide isolator is surrounded by an insulating sleeve.

31. The isolating circuit according to claim 25 including a microwave choke mounted on the RF connector to prevent the microwave EM energy from leaking out of the waveguide isolator through the signal conductor of the RF connector.

32. The isolating circuit according to claim 31, wherein the microwave choke is radial or cylindrical.

* * * * *